US012773388B2

(12) United States Patent
Dalko et al.

(10) Patent No.: US 12,773,388 B2
(45) Date of Patent: Oct. 27, 2026

(54) STIMULI - OR BIO-RESPONSIVE COPOLYMERS, THE POLYMERSOMES COMPRISING THE SAME AND THEIR USE IN DRUG DELIVERY

(71) Applicants: CENTRE NATIONAL DE LA RECHERCHE SCIENTIFIQUE, Paris (FR); INSTITUT POLYTECHNIQUE DE BORDEAUX, Talence (FR); Ecole Nationale Supérieure de Chimie de Paris, Paris Cedex (FR); INSTITUT NATIONAL DE LA SANTE ET DE LA RECHERCHE MEDICALE (INSERM), Paris (FR); UNIVERSITÉ DE BORDEAUX, Bordeaux (FR); UNIVERSITE PARIS CITE, Paris (FR)

(72) Inventors: Peter I. Dalko, Orsay (FR); Olivier Sandre, Pessac (FR); Grégory Ramniceanu, Tel Aviv (IL); Sébastien Lecommandoux, Canejan (FR); Zoeisha Chinoy, Pessac (FR); Bich-Thuy Doan, Carrieres sur Seine (FR); Petra Dunkel, Budapest (HU); Amit Kumar, Paris (FR)

(73) Assignees: CENTRE NATIONAL DE LA RECHERCHE SCIENTIFIQUE, Paris (FR); INSTITUT POLYTECHNIQUE DE BORDEAUX, Talence (FR); Ecole Nationale Supérieure de Chimie de Paris, Paris Cedex (FR); INSTITUT NATIONAL DE LA SANTE ET DE LA RECHERCHE MEDICALE (INSERM), Paris (FR); UNIVERSITÉ DE BORDEAUX, Bordeaux (FR); UNIVERSITE PARIS CITE, Paris (FR)

( * ) Notice: Subject to any disclaimer, the term of this patent is extended or adjusted under 35 U.S.C. 154(b) by 619 days.

(21) Appl. No.: 17/784,139

(22) PCT Filed: Dec. 10, 2020

(86) PCT No.: PCT/EP2020/085615

§ 371 (c)(1),
(2) Date: Jun. 10, 2022

(87) PCT Pub. No.: WO2021/116331

PCT Pub. Date: Jun. 17, 2021

(65) Prior Publication Data

US 2023/0093684 A1 Mar. 23, 2023

(30) Foreign Application Priority Data

Dec. 10, 2019 (EP) .................................... 19306612

(51) Int. Cl.

| | |
|---|---|
| ***A61K 9/1273*** | (2025.01) |
| ***A61K 31/704*** | (2006.01) |
| ***A61K 41/00*** | (2020.01) |
| ***A61K 49/00*** | (2006.01) |
| ***A61K 49/18*** | (2006.01) |
| ***C08G 81/00*** | (2006.01) |

(52) U.S. Cl.

CPC .......... *A61K 9/1273* (2013.01); *A61K 31/704* (2013.01); *A61K 41/0028* (2013.01); *A61K 49/0086* (2013.01); *A61K 49/1812* (2013.01); *C08G 81/00* (2013.01)

(58) Field of Classification Search

None

See application file for complete search history.

(56) References Cited

FOREIGN PATENT DOCUMENTS

| | | |
|---|---|---|
| WO | 2010049611 A1 | 5/2010 |
| WO | 2017173453 A1 | 10/2017 |

OTHER PUBLICATIONS

Xin Mu et al, "Stimulus-responsive vesicular polymer nano-integrators for drug and gene delivery", International Journal of Nanomedicine, vol. vol. 14, Jul. 1, 2019 (Jul. 1, 2019), p. 5415-5434.

*Primary Examiner* — Nissa M Westerberg

(74) *Attorney, Agent, or Firm* — Greer, Burns & Crain, Ltd.

(57) ABSTRACT

The present invention concerns amphiphilic copolymers that may be photo- or redox-cleavable and that may assemble into polymersomes. It also concerns their process of preparation and their use as drug carriers.

12 Claims, 12 Drawing Sheets

FIG.5
no reduced
0,0 min
10,0 min
20,0 min
30,0 min
Fluorescence
6000
5000
4000
3000
2000
1000
0
520
570
620
670
720
Wavelength (nm)

FIG.11
28288
50 ms
2121
48h
24h
6h
2h
1h
T0
liver
liver
Spleen
Supine position
Left side

STIMULI - OR BIO-RESPONSIVE COPOLYMERS, THE POLYMERSOMES COMPRISING THE SAME AND THEIR USE IN DRUG DELIVERY

The present invention concerns the field of polymersomes, and their uses in therapeutics.

Polymersomes are artificial vesicles that may vehicle an aqueous solution in the core, surrounded by a bi-layer membrane. These carriers are prepared by the self-assembly of amphiphilic block copolymers containing two or more chemically distinct (monomer) sequences joined by a covalent bond that prevents phase separation of the blocks upon dissolution. Due to their hollow and spherical morphology, polymersomes are capable of encapsulating various agents within the vesicle core or in the hydrophobic bilayer depending on the characteristics of the payload. The aqueous core of polymersomes is separated from the outside medium by a hydrophobic membrane, which makes them a vesicle-like structure with an aqueous inner core surrounded by a hydrophobic shell. Thus, this makes them suitable as drug carriers for hydrophilic substances (in the lumen) and hydrophobic substances (in the membrane) possibly offering a multipurpose cocktail-treatment or a diagnostic-therapy combination for biomedical applications. In particular, scientific literature contains several descriptions of the insertion of magnetic iron oxide nanoparticles coated with a hydrophobic surfactant shell within the membranes of polymersomes (Lecommandoux et al, Adv. Mat 17 (6), 712-718 (2005)). Polymersomes that are degradable by pH or by enzymatic route (esterases) have been reported earlier (Mu et al, International Journal of Nanomedicine 2019:14 5415-5434).

According to the most common delivery strategies, hydrophobic blocks can be progressively degraded, or, converted into hydrophilic substances, or, cleavable linkages are incorporated between hydrophobic and hydrophilic blocks. As the degradation and thus the delivery are based on similar concepts than those used in other prodrug strategies, the passive release i.e. utilization of the target tissue physiology for the delivery of the active compounds suffers similar shortcomings, and is often very slow.

It is therefore desirable to provide alternative strategies for active delivery.

The invention provides stimuli- or bio-responsive polymersomes including a photo- or redox-sensitized composite that may release their content only at the site of action, upon an external stimulus, compatible with therapeutic considerations, or an endogenous stimulus (e.g. peculiar redox potential of tumor microenvironment). These nano-materials undergo chemical bond fragmentation by local electron-transfer (ET) reaction, generated by e.g. the interaction of X-ray/gamma rays, water, and photosensitizing nanoparticles embedded within the polymeric composite matrix.

The present invention thus proposes a novel type of delivery method that may trigger remotely these nanoparticles in high spatial (local) selectivity, resulting in diminished (general) toxicity of the payload. It thus provides a drug delivery system that allows space and time-controlled release of an (active) compound in otherwise inaccessible (body) spaces.

According to an object, the present invention provides a photo- or redox-cleavable amphiphilic copolymer compound of formula (I):

(I)

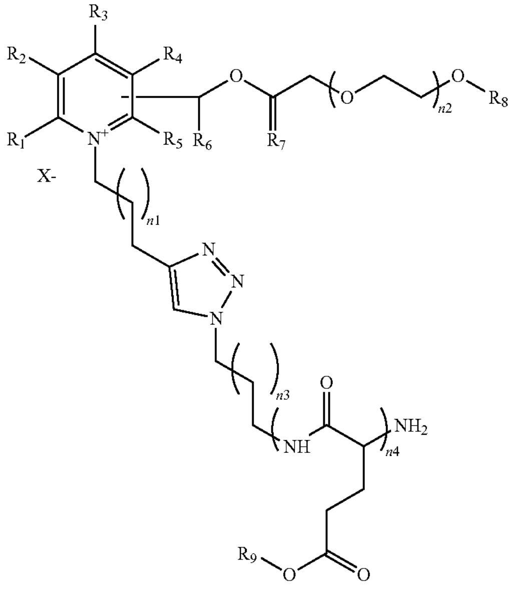

Where:

The side chain

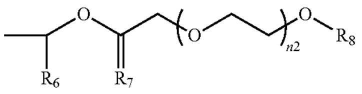

is located at any position of the $R_1$, $R_2$, $R_3$ $R_4$ and $R_5$, wherein said $R_1$, $R_2$, $R_3$ $R_4$ and $R_5$ is then absent;

- When present, $R_1$, $R_2$, $R_3$ $R_4$ and $R_5$ are substitution groups on the pyridinium ring and are chosen from H, OH, OMethyl, CN, $NR_2$, $NO_2$, halogen, or two adjacent $R_1$, $R_2$, $R_3$ $R_4$ and $R_5$ are linked together to form one or more aromatic rings fused with the pyridinium ring to which they are attached so as to form an optionally bi-cyclic substituted quinolinium or an optionally substituted fused tri-cyclic N-containing heteroaryl (e.g. acridinium),
- $R_6$ is H or an alkyl group;
- $R_7$ is O or alkylene;
- $R_8$ and $R_9$ identical or different are independently chosen from H, alkyl, aryl or benzyl, preferably methyl or benzyl;
- $n_1$ and $n_3$ are identical or different integers comprised between 0 and 5 defining the length of the spacer;

$n_2$ is an integer comprised between 34 and 80 denoting the polymerization degree of ethylene oxide in the hydrophilic block of the amphiphilic copolymer;

$n_4$ is an integer chosen between 18 and 40 denoting the polymerization degree of benzyl-L-glutamate in the hydrophobic block of the amphiphilic copolymer;

$X^-$ is a halide or a trifluoromethanesulfonate (—OTf), phosphate, sulfate, perchlorate or nitrate ion;

or an alternative pharmaceutically acceptable salt thereof.

The term "photo- or redox-cleavable" means that the copolymer may be cleaved i.e. dissociated into fragments by a stimulus chosen from UV light, visible or near infrared photon (photodynamic), ionizing (beta ray, X-ray or gamma) irradiation, ultrasound or an endogenous or exogenous redox activation.

Typically, the copolymer may be fragmented so as to release each of the side chains substituted on the N-containing heterocyclic core.

As used herein, "amphiphilic" designates the capacity of the copolymer to exhibit both hydrophilic and lipophilic (or hydrophobic) properties and subsequently the ability to self-assemble into multi-molecular objects dispersed in pure water or in aqueous solutions.

"Halo", "hal" or "halogen" refers to fluorine, chlorine, bromine or iodine atom.

"Halide" refers to the anion of a halogen atom.

"Alkyl" represents an aliphatic-hydrocarbon group which may be straight or branched having 1 to 6 carbon atoms in the chain. In a particularly preferred embodiment, the alkyl group has 1 to 4 carbon atoms in the chain. Exemplary alkyl groups include methyl, ethyl, n-propyl, iso-propyl, iso-butyl, n-butyl, tert-butyl, n-pentyl, 3-pentyl.

Alkylene refers to an alkyl group where two hydrogen atoms have been removed at the same carbon atom, so as to have two valencies in the form of a terminal double bond, available for attachment. As illustrated for R7, it may represent a $CH_2$ or $CH_2—CH_3$, attached to C through a double bond.

"Aryl" designates an aromatic, mono or bicyclic group comprising between 5 and 10 carbon atoms, such as phenyl or naphthyl.

"Heteroaryl" corresponds to an aromatic, mono, bi or tricyclic group comprising between 3 and 15 carbon atoms and between 1 and 10 heteroatoms, such as nitrogen, oxygen or sulfur atoms. Examples of such heteroaryl groups include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, acridinyl, etc.

"Benzyl" abbreviated as "Bn" designates an -Alkyl-phenyl group, where Alkyl is defined as above.

In the formula (I), the poly(ethylene oxide) block exhibits hydrophilic properties, while the

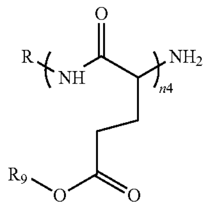

poly(glutamate) moiety exhibits lipophilic properties in particular if $R_9$ is different from H (i.e. the side chains forms an ester bond, although poly(glutamic acid) can also form hydrophobic alpha-helices structures when the carboxylic group is protonated, i.e. at acidic pH below its pKa).

Preferably, in general formula (I):

$R_5$ is absent and the side chain

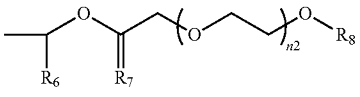

is located on the $R_5$ (ortho) position; and/or $R_1$, $R_2$, $R_3$ and $R_4$ represent H, or $R_1$, $R_2$ are linked together to form a phenyl ring fused with the pyridinium ring to which they are attached so as to form an optionally substituted quinolinium and $R_3$ and $R_4$ are H; and/or $R_6$ is H or methyl;

$R_7$ is O, or —($CH{=}R_7$)— represents —($CH{=}CH_2$)—, and/or $R_8$ and $R_9$ identical or different are independently chosen from alkyl or benzyl, more preferably $R_a$ is alkyl, such as methyl, and $R_9$ is benzyl; and/or $n_1$ and $n_3$ are identical or different integers comprised between 0 to 5; and preferably equal to 1 or 2, defining the length of the spacer; and/or $n_2$ is an integer comprised between 34 and 80 denoting the polymerization degree of ethylene oxide in the hydrophilic block of the amphiphilic copolymer; and/or $n_4$ is an integer chosen between 18 and 40, more preferably 20-35; and/or $X^-$ is a halide or a trifluoromethanesulfonate ($OTf^-$) ion.

According to an embodiment, the copolymer compound of formula (I) may be chosen from the compounds of formulae:

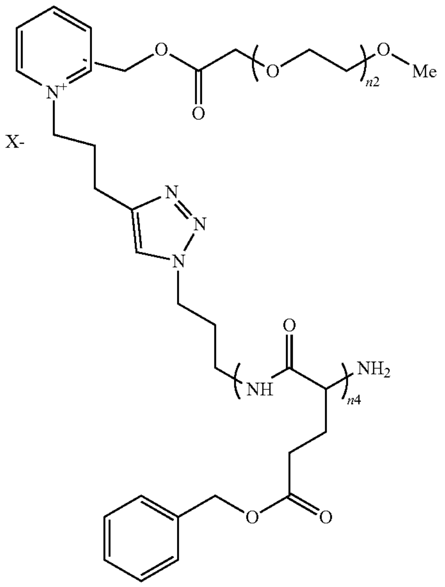

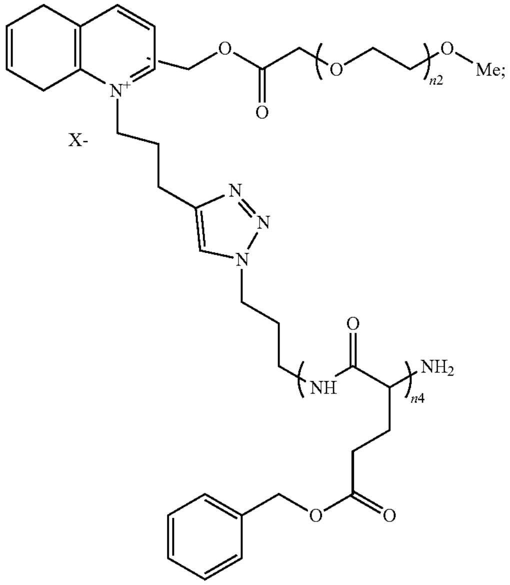

more preferably from the following compounds:

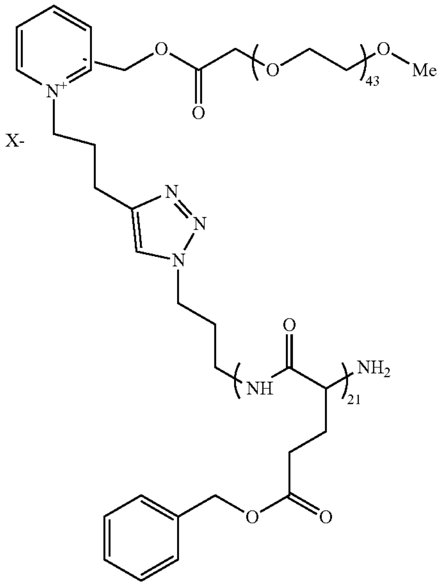

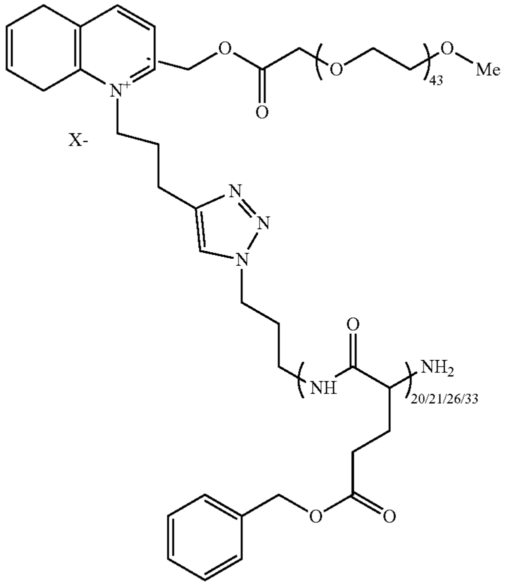

Where $X^-$ is a halide or a trifluoromethanesulfonate ($OTf^-$),

And the alternative pharmaceutically acceptable salts thereof.

The compounds of Formula (I) comprise amphiphilic diblocks, such as poly(benzyl-L-glutamate) (PBLG) as the hydrophobic block (prepared from the corresponding L-amino acid N-carboxyanhydride (NCA) by ring-opening polymerization (ROP), and such as poly(ethylene glycol) (PEG) also called poly(ethylene oxide) (PEO) as the hydrophilic block. These blocks are assembled by chemical bond coupling around a redox-sensitive linker derived from N-alkyl heterocycles, such as picolinium, or, quinolinium derivatives.

The present invention includes salts of compounds of formula (I). The salts may preferably be pharmaceutically acceptable salts. Lists of suitable salts may be found in Remington's Pharmaceutical Sciences, 17th ed., Mack Publishing Company, Easton, PA, 1985, p. 1418 and P. H. Stahl, C. G. Wermuth, *Handbook of Pharmaceutical salts—Properties, Selection and Use*, Wiley-VCH, 2002, the disclosures of which are hereby incorporated by reference. These salts are advantageously prepared with pharmaceutically acceptable acids, but salts with other acids, useful for example for the purification or for the isolation of the compounds of formula (I), also form part of the invention.

The compounds of formula (I) can comprise one or more asymmetric carbon, in particular the α carbon of the amino acid benzyl-glutamate that is preferably in its natural L configuration, hence the PBLG denomination for the block. However they can exist in the other forms of enantiomers or diastereoisomers. These enantiomers and diastereoisomers, as well as their mixtures, including racemic mixtures, form part of the invention. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

According to a further object, the present invention also concerns the process of preparation of the copolymer of formula (I), said process comprising the step of reacting a compound of formula (II):

(II)

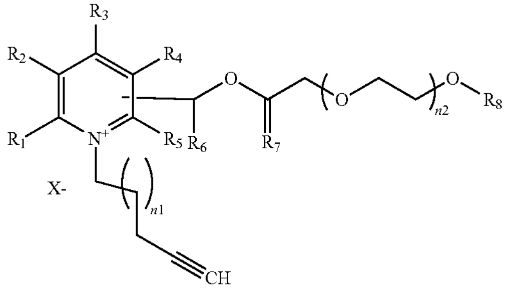

with a compound of formula (III)°:

(III)

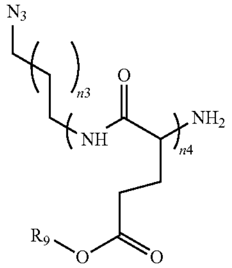

Wherein $R_1$, $R_2$, $R_3$ $R_4$, $R_5$, $R_6$, $R_7$, $R_8$, $R_9$, R, X, $n_1$, $n_2$ $n_3$ and $n_4$ are defined as in formula (I).

The compounds of the present invention and intermediates thereof may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations, VCH publishers,* 1989. The reagents and starting materials may be commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups herein named Pg may be used in accordance with standard practice, for examples see T. W. Greene and P. G. M. Wuts in *Protective Groups in Organic Synthesis*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethyl-formamide; alcohols such as ethanol and methanol and ethers, such as diethyl ether and tetrahydrofuran.

The reactions can take place over a wide range of temperatures. In general, it was found convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, precipitation, or by various chromatography techniques, notably column chromatography or preparative thin layer chromatography.

Generally, the starting products and the reagents described herein are commercially available or can be prepared according to the examples, or by application or adaptation of known methods.

According to a further object, the invention also concerns an aqueous suspension of polymersomes comprising an amphiphilic bilayer, wherein the amphiphilic bilayer of said polymersomes comprise a photo-cleavable or redox-cleavable amphiphilic copolymer compound and embedded nanoparticles acting both as photosensitizers and contrast agents for image-guided therapy according to the invention.

Said polymersome is also called herein "amphiphilic copolymer vesicle".

The present invention also concerns the preparation of polymersomes. The compounds of the invention may be able to self-assemble into a polymersome suspension in water (i.e) a large number such as hundreds of millions of polymersomes per microliter suspended in an aqueous buffer (as typically measured with the qNano counter instrument ilZON Science inc.), by means of the amphiphilic nature of the building blocks of the macromolecules (e.g. having large hydrophilic and hydrophobic terminals) for which water acts a "selective solvent" (i.e. a good solvent of one block only and a bad solvent for the other one). Amphiphilic compounds are known to undergo self-assembly into a wide range of morphologies like spheres, cylinders, continuous structure, lamella, vesicles or many other complex shapes/assemblies. The hydrophilic and hydrophobic blocks of Formula (I) allows self-assembly by forming polymersomes, in particular thanks to the antagonist miscibility in aqueous environment of both blocks. Among different self-assembly processes, nanoprecipitation also called 'solvent shift' or 'solvent displacement' method consists in adding a selective solvent, usually water, that is a good solvent for one block and a bad solvent for the other block, to a copolymer solution initially dissolved in a non-selective solvent or common solvent (THF, DMSO, acetone, alcohol . . . ) that is a good solvent of both blocks and that, in addition, is itself miscible with water. After the process, the excess of solvent mixed with water is eliminated either by slight heating (e.g. 40° C. overnight) or by dialysis in a tube with a semi-permeable membrane that is equilibrated with an aqueous solution (pure water, pH buffer, saline, cell culture medium, blood plasma, etc.).

Sizes and morphologies of polymersomes can be controlled by varying the chemical constitution and block length of the co-polymer, e.g. by the chemical step, but also by the preparation method or self-assembly process, e.g. by controlling the properties of the initial co-polymer solution such as concentration, temperature, and solvent type, pH and salinity of the aqueous phase, etc., and by the mixing conditions (stirring velocity, fast addition or slow addition, at controlled flowrate, water-in-solvent addition or reverse order, macroscopic container or microfluidic reactor . . . ) as referenced for instance in C. Sanson, C. Schatz, J-F. Le Meins, A. Brûlet, A. Soum, S. Lecommandoux, Langmuir 2010, 26, 2751-2760.

According to the invention, polymersomes may be prepared in the size range of tens of nanometers to less than 10 micrometers of diameter. Typically, the average diameter is comprised between 50 nm and 1 micrometer, as determined by the so-called $2^{nd}$ order Cumulant fitting method of the dynamic light scattering (DLS) curves.

The envelope bilayer is generally 10 to 30 nm thick, as measured by electron microscopy or by a small angle scattering technique (X-ray or neutrons, respectively SAXS or SANS).

Typically, the polymersome suspension of the invention exhibits narrow size distribution width, of about 80-140 nm of hydrodynamic radii with polydispersity index (PDI) between 0.10 and 0.25 as measured by DLS, and/or correlated to other types of hydrodynamic size analysis such as Coulter counter or nanoparticle tracking (NTA). The nanoscale structure of the polymersomes may be ascertained by transmission (TEM) or scanning (SEM) and/or cryogenic (cryo-TEM) electron microscopy image analyses, with or without positive or negative sample staining, or by atomic force microscopy (AFM). They may be characterized also by small angle X-ray scattering (SAXS), small angle neutron scattering (SANS), asymmetric flow (A4F) or field-flow fractionation (FFF) chromatography or multi-angle static and dynamic light scattering (MALS) techniques to determine the radius of gyration ($R_g$) in addition to the hydrodynamic radius ($R_h$) of the self-assemblies. Then the so-called ρ-ratio of $R_g$ over $R_h$ enables discriminating vesicular (shell-like) structure by a value close to 1, as opposed to values close to $\sqrt{(3/5)}$~0.77 for filled spherical micelles or reaching up to 2 for elongated (rod-like) cylindrical micelles. These procedures may be conducted by application or adaptation of known methods in colloidal science.

According to an embodiment, said polymersome structure further comprises a significant number of (semi-)metal or metal oxide or other metal chalcogenide (sulfide, telluride . . . ) nanoparticles embedded into said polymersome membrane, constituting a significant feed weight ratio (FWR) relatively to the total polymer weight, typically from 5% to 50%, and preferentially between 10% and 20%.

Typically, said mineral i.e. non-organic metal, semi-metal, metal oxide or chalcogenide, alkaline earth or rare earth may be chosen from the d group consisting of a transition metal or an element of another family yet with an atomic number greater than 21, a noble metal (silver, gold, platinum . . . ), a metal alloy, or a lanthanide of the f-group of the periodic table of the elements.

According to a further embodiment, said mineral (metal, semi-metal, metal oxide, chalcogenide, or an earth) nanoparticle is an ultra-small iron oxide nanoparticle (USPIO), a superparamagnetic iron oxide nanoparticle (SPION), a very small iron oxide nanoparticles (VSION), a hafnium-oxide, an iron-bismuth or iron-platinum alloy, a gadolinium oxide, silver, platinum, or a gold nanoparticle or atom cluster.

Superparamagnetic iron oxide nanoparticles (SPION) are typically used as MRI contrast agents and are composed of nano-sized iron oxide crystals coated with dextran or carboxydextran. The principal effect of USPIO or SPION particles is on $T_2$* relaxation and thus magnetic resonance (MR) imaging is usually performed using $T_2/T_2$*-weighted sequences in which the tissue signal loss is due to the susceptibility effects of the superparamagnetic iron oxide core. Beyond their MR imaging capacity, USPIO and SPION nanoparticles are studied in cancer therapy. USPIOs showed interesting radiation dose deposit profile in the past, some of them by intracellular manner. Iron oxide nanoparticles (USPIOs or SPIONs) for example allow bio-distribution study by in vivo MRI and EPR (enhanced retention effect) monitored by MRI. In addition to regular SPIONs usually used as negative ($T_2/T_2$*-type) MRI contrast agents, there exists also very small iron oxide nanoparticles (VSION), with diameters around 4±1 nm, that can be used as positive contrast agents (signal enhancer) in combination with $T_1$-weight sequences, in particular for MRI angiography [T Vangijzegem, D Stanicki, S Boutry, Q Paternoster, L Vander Elst, R N Muller, S Laurent, Nanotechnology 29, 2018, 265103]

USPIO, SPION and VSION nanoparticles may act both as MRI contrast agents, and as X-ray or F-ray photosensitizers. This may allow for in vivo bio-distribution studies such as for mapping tumors by MRI, before applying conventional radiotherapy. These polymersomes may be used for encapsulation of reporters, such as near infrared (NIR) fluorescent dyes, or, active pharmaceutical ingredients (API). They thus may be useful for monitoring the bio-distribution and studying the activation of stimuli-sensitive polymersomes.

According to a still further embodiment, said polymersomes may further comprise a API, said API being encapsulated within either the aqueous compartment or within the hydrophobic membrane of said polymersomes, depending on water solubility of said API.

The API encapsulated by the polymersomes may be chosen from APIs for the treatment of cancer, immune-related diseases, inflammation, diabetes, bacterial and/or viral infections, and orphan diseases, pediatric or age-related diseases, such as sorafenib, doxorubicin, monomethyl auristatin E (MMAE), cisplatin, or combrestatin.

The invention also concerns the process of preparation of the polymersomes of the invention.

According to the invention, the polymersomes, optionally comprising the API and/or the mineral (metal or metal oxide) nanoparticles may be obtained by self-assembly. Typically, this may be achieved by solvent displacement, by application or adaptation of the methodology disclosed by Sanson et al ACS Nano, 2011, 5, 1122-1140. According to an embodiment, this may be conducted in mixture of water and a miscible organic solvent such as tetrahydrofuran (THF), dimethylsulfoxide (DMSO), acetone, isopropylalcohol (iPrOH), ethanol (EtOH), acetonitrile (ACN), dimethylformamide (DMF) or ethylacetate (EtOAc). Typically, the mixture comprises between 10 and 70% v/v of the organic solvent and between 30 and 90% of water.

Polymersomes whose membranes comprise a significant weight fraction of mineral (metal or metal oxide) nanoparticles may be prepared by water displacement methodology, advantageously, by using lipophilic surfactants (such as phosphoric ester of poly(ethylene oxide)$_9$ nonylphenyl ether) sold under brand name Beycostat™ typically for the metal oxide nanoparticle such as ultra-small iron oxide particle (USPIO) coating or poly(2-vinyl pyridine) (P2VP) for silver or gold nanoparticle coating and dispersion in THF.

According to a further object, the present invention concerns an aqueous suspension comprising polymersomes according to the invention.

According to a still further object, the invention also provides for the process of preparation of the suspension of polymersomes of the invention, said process comprising the steps of:

- Optionally mixing a compound of formula (I) with a hydrophobically coated metal or metal oxide nanoparticle suspension and/or a API in an organic solvent miscible with water
- Self-assembly by nanoprecipitation of the polymersome vesicles in an aqueous solution (also called "solvent-shift" method), optionally followed by
- dialysis or heating of the suspension to remove any trace of organic solvent.

Said water-miscible solvent may be typically chosen from THF, DMSO, DMF, acetonitrile, acetone, ethyl acetate, or various alcohols.

According to a still further object, the present invention also concerns a pharmaceutical composition or a medical device comprising an aqueous suspension of the invention.

According to a further object, the present invention also concerns the use of the photo-cleavable or redox-cleavable amphiphilic copolymer compound, the polymersome, the suspension of polymersomes, the medical device or the pharmaceutical composition of the invention as a contrast agent for biomedical imaging.

Said contrast agent may be particularly suitable for a bio-imaging modality, optical endoscopy, ultrasound echography, magnetic resonance imaging (MRI), X-ray scanner also called computed tomography (CT), particularly when comprising an API for the image-guided treatment of a disorder. Said treatment may typically comprise:

- the implantation of said medical device at a disorder site or the systemic administration of said compound, polymersome, suspension of polymersomes or pharmaceutical composition;
- the activation of the compound of formula (I) at the targeted site by either an externally applied mean or an endogenous signal, thereby releasing the API at the targeted site; and
- optionally monitoring the distribution of the mineral (metal or metal oxide) nanoparticles embedded in polymersomes within the human body.

Typically, the activation may be achieved by the cleavage of the polymersome membrane, said cleavage being induced by UV light, visible photon (photodynamic), ionizing (beta ray, X-ray or gamma-ray) irradiation, focused ultrasound (FUS), or, either endogenous or exogenous redox activation at the targeted site. Therefore, the activation may be carried out by beta rays, X rays or gamma rays irradiation, or by exploiting endogenous signals such as redox enzymes, metalloproteases, reactive oxygen species (ROS) like peroxides or reactive nitrogen species (NO•). The activation i.e. the external (trigger) signal may affect some physicochemical e.g. rheological (i.e. fluid-like) or permeability parameters of the membrane, and the structure or morphology of the polymersomes of the invention. The modification can affect the ratio between the hydrophilic or hydrophobic blocks, the solubility of the membrane components, the degradation or bond cleavage of the macromolecules, which would result in changes of their aggregation features at the supra-macromolecular level. The response to the stimuli might be reversible, or, irreversible, depending on the employed approach.

The local activation leads to minimized toxicity to vital tissues and organs away from the target. The combination of intracellular high-energy dose deposit and of the local liberation of chemical API substances opens new protocols in cancer personalized therapy and may change the benefit/risk ratio in radiotherapy.

Typically, the monitoring may be achieved by a non-invasive bio-imaging technique such as MRI with a magnetic metal or metal oxide or lanthanide (Gd, Dy . . . ), optical modalities (visible or near-infrared fiber optic endoscopy or photoluminescence with quantum dots (QD) or lanthanide doped up-converting nanoparticles (UCNP), positron emission tomography (PET), single photon emission computed tomography (SPECT) with a radionuclide, or X-ray computed tomography with an element of atomic number higher than 21 or with a halogen, such as iodine, or fluorine for $^{19}F$ MRI with triflate as the counter-anion of the quaternarized heterocycle such as pyridinum, quinolinium ring.

The method of the invention relies on the generation of local electrons (Auger-, or Compton-electrons) formed by the interaction of high energy electromagnetic wave (X-rays/gamma-rays) and metal-derived nanoparticles embedded in the polymeric matrix. Besides, in the case of a magnetic transition metal (e.g. iron) or magnetic lanthanide (e.g. gadolinium, dysprosium, . . . ) the proton relaxivity properties of the resulting MRI contrast agent is high, leading to high efficacy for in vivo MRI for image guided study or therapy. Otherwise, high atomic number atoms (e.g. iodine, silver, gold, barium, bismuth . . . ) can provide absorption or phase contrast for imaging by computed (X ray) tomography.

The disorder may be chosen in particular from cancer, immune-related diseases, inflammation, diabetes, bacterial and/or viral infections, pediatric or age-related diseases.

According to a further embodiment, the present invention also concerns a method of treatment and/or prevention of a disorder chosen from cancer, immune-related diseases, inflammation, diabetes, bacterial and/or viral infections, pediatric or age-related diseases comprising the administration of a compound of formula (I) according to the invention as defined above to a patient in the need thereof.

As used herein, the term "patient" refers to a warm-blooded animal such as a mammal, preferably a human or a human child, which is afflicted with, or has the potential to be afflicted with one or more diseases and conditions described herein.

As used herein, a "therapeutically effective amount" refers to an amount of a compound of the present invention, which is effective in reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment and chronic use.

As used herein, the expression "pharmaceutically acceptable" refers to those compounds, materials, compositions, or dosage forms, which are, within the scope of sound medical judgment, suitable for contact with the tissues of human beings and animals without excessive toxicity, irritation, allergic response, or other problem complications commensurate with a reasonable benefit/risk ratio.

In the context of the invention, the term "treating" or "treatment", as used herein, means reversing, alleviating, inhibiting the progress of, or preventing the disorder or condition to which such term applies, or one or more symptoms of such disorder or condition.

The dosage of the API to be administered depends on such variables as the type and extent of progression of the disease or disorder, the overall health status of the particular patient, the relative biological efficacy of the compound selected, and formulation of the compound, excipients, and its route of administration.

Compounds of the present invention may be formulated into a pharmaceutically acceptable preparation, on admixing with a carrier, excipient or a diluent, in particular for oral or parenteral use. Oral preparations may be in the form of tablets, mini-tablets, capsules, topical or parenteral. A solid carrier can include one or more substances which may also act as flavoring agents, lubricants, solubilizers, suspending agents, fillers, glidants, compression aids, binders or tablet-disintegrating agents; it can also be an encapsulating material. Liquid carriers can include water, an organic solvent, a mixture of both or pharmaceutically acceptable oils and fats (e.g. medium-chain triglycerides). The compositions may conveniently be administered in unit dosage form and may be prepared by any of the methods well known in the pharmaceutical art, for example, as described in Remington: The Science and Practice of Pharmacy, 20th ed.; Gennaro, A. R., Ed.; Lippincott Williams & Wilkins: Philadelphia, PA, 2000. Pharmaceutically compatible binding agents and/or adjuvant materials can be included as part of the composition. The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Preferred tablets contain lactose, cornstarch, magnesium silicate, croscarmellose sodium, povidone, magnesium stearate, or talc in any combination. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, acrylate copolymers, vegetable oils such as olive oil, and organic esters such as ethyl oleate. Aqueous carriers include mixtures of alcohols and water, hydrogels, buffered media, and saline. In particular, biocompatible, biodegradable L-lactide polymer (PLA), L-lactide-co-glycolide copolymer (PLGA), or poly(ethylene oxide)-co-poly(propylene oxide) copolymers may be useful excipients to control the release of the API. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, hydrogels and liposomes.

Other features of the invention will become apparent in the course of the following description of exemplary embodiments that are given for illustration of the invention and not intended to be limiting thereof.

Cuvette: quartz, d (light path): 1 mm, Beam energy: 120 keV, Bunch length: 48 ps, Bunch repetition rate 5.68 MHz, Dose: 30 Gy).

Figure 8:
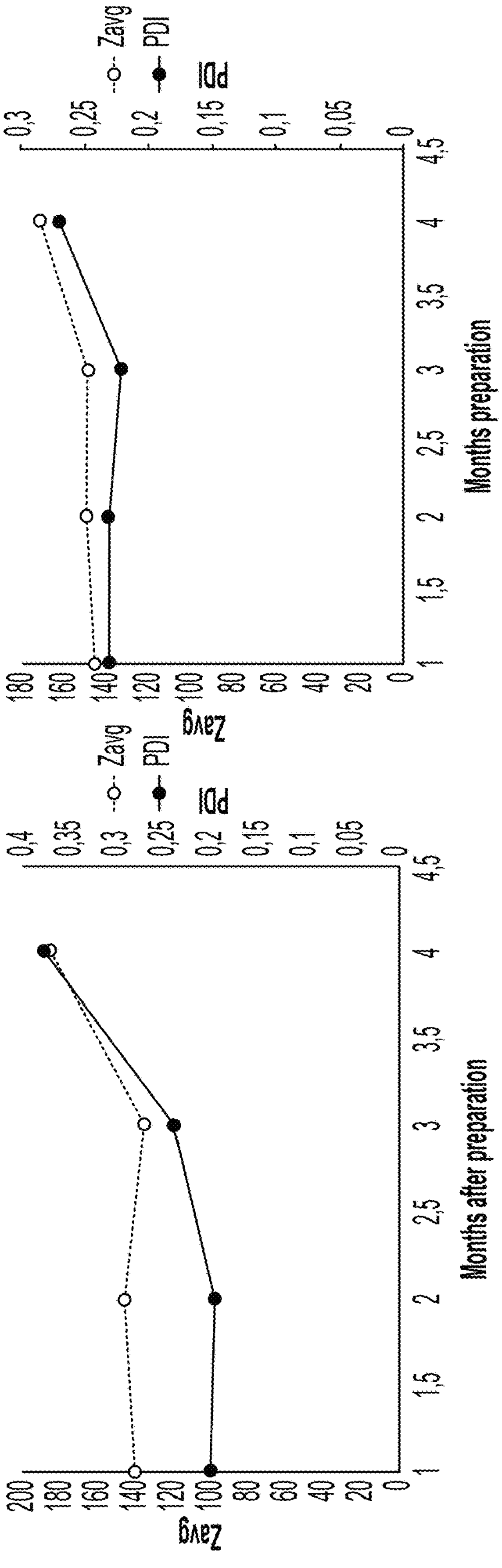

FIG. 8. Variation in hydrodynamic diameter (Zavg diameter and PDI) of Quino-Ps (A) and Quino-Ps(Fe) (B) as measured by DLS.

Figure 9:
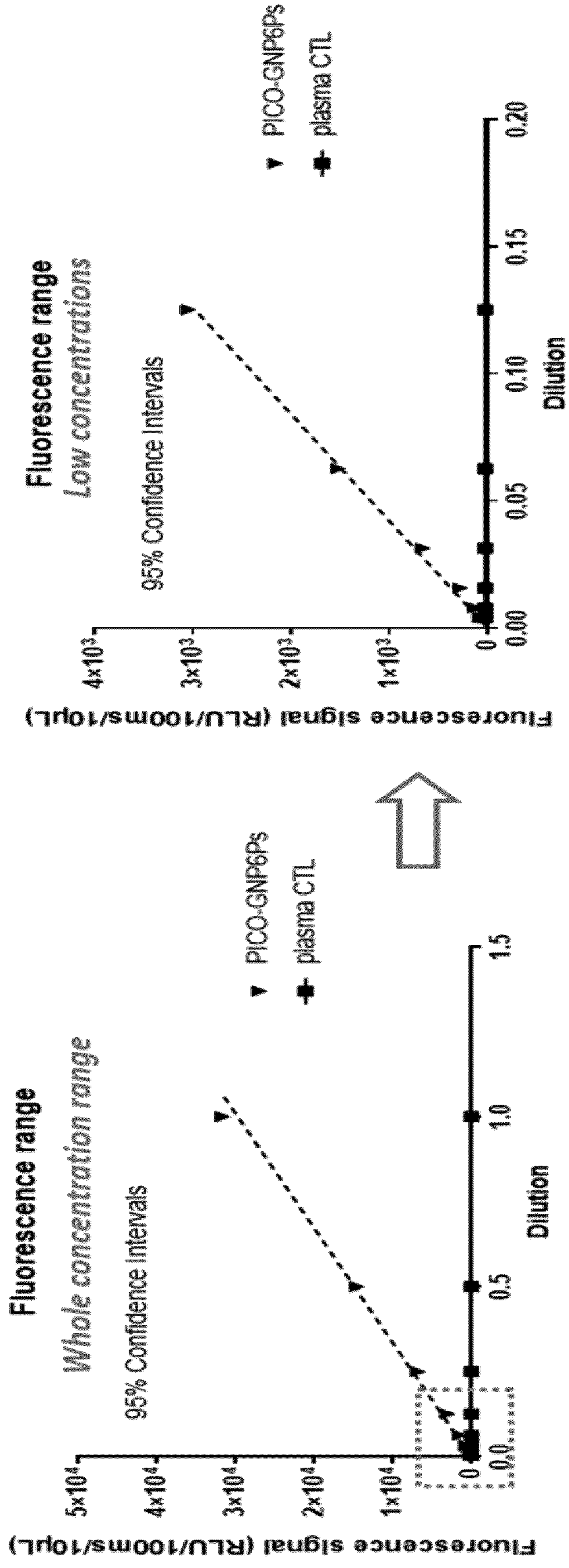

FIG. 9: In vitro fluorescence signal obtained with varying concentrations of PICO-GNP6Ps.

Figure 10:
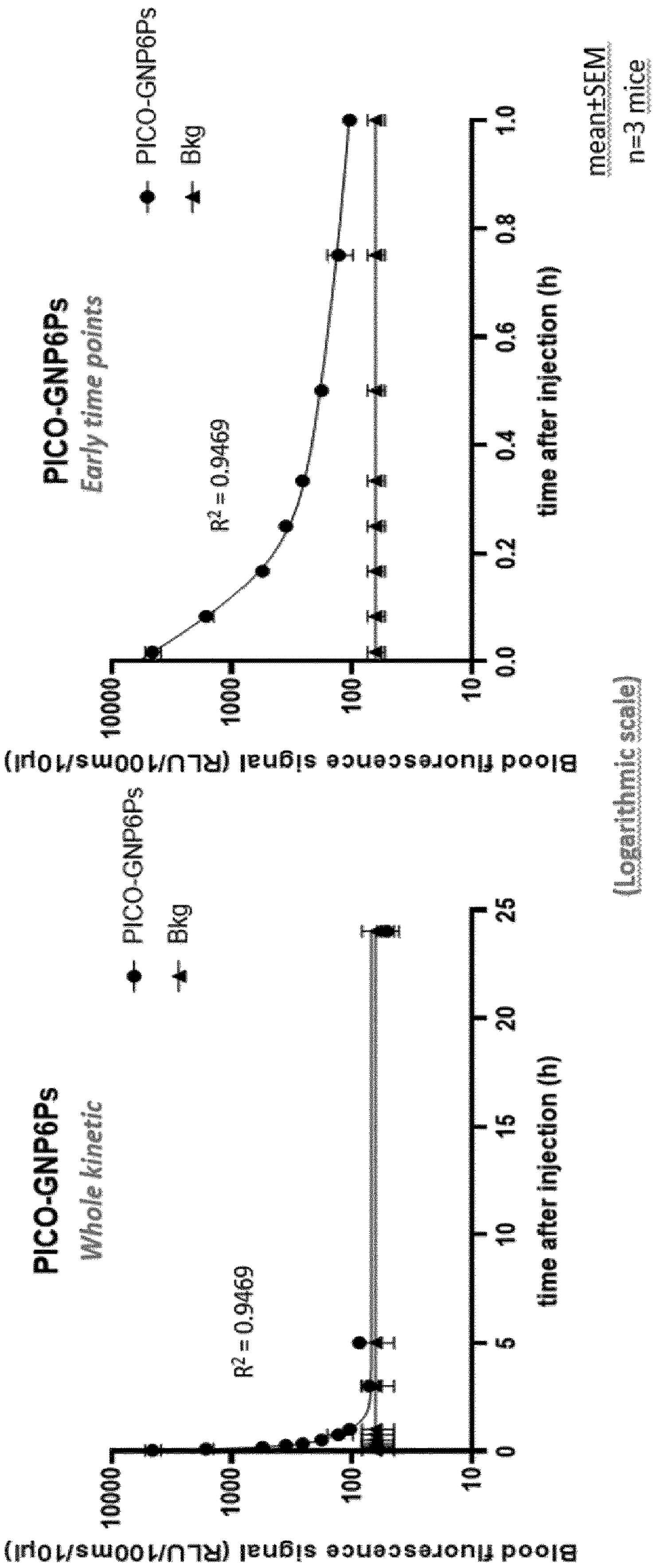

FIG. 10: In vivo blood fluorescence signal over time after injection of PICO-GNP6Ps in mice.

Figure 11:

FIG. 11: In vivo fluorescence imaging of PICO-GNP6Ps.

Figure 12:
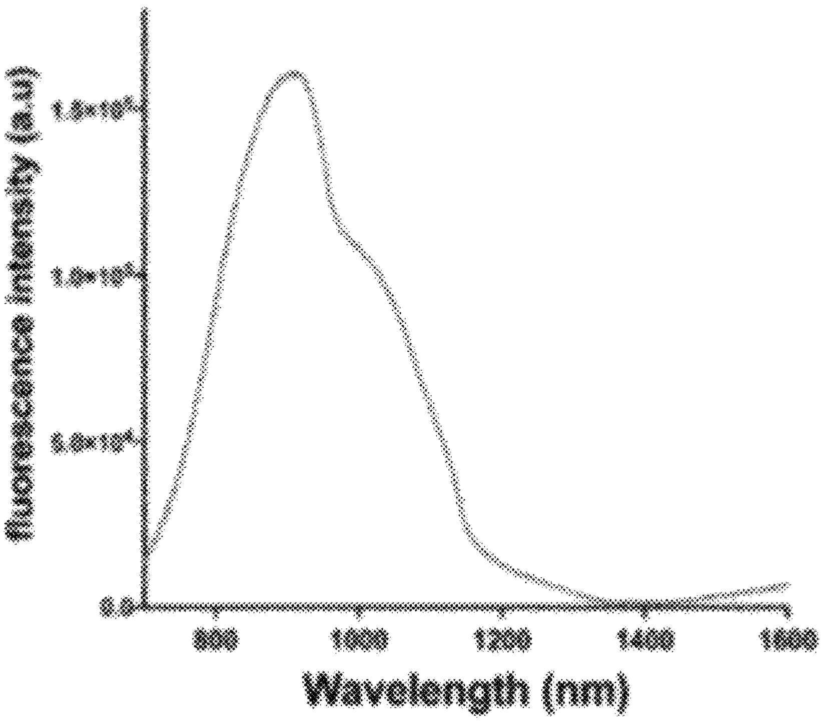

FIG. 12: The fluorescence spectrum of GNP-modified picolinium NPs ($\lambda_{ex}$=400 nm).

Figure 13:
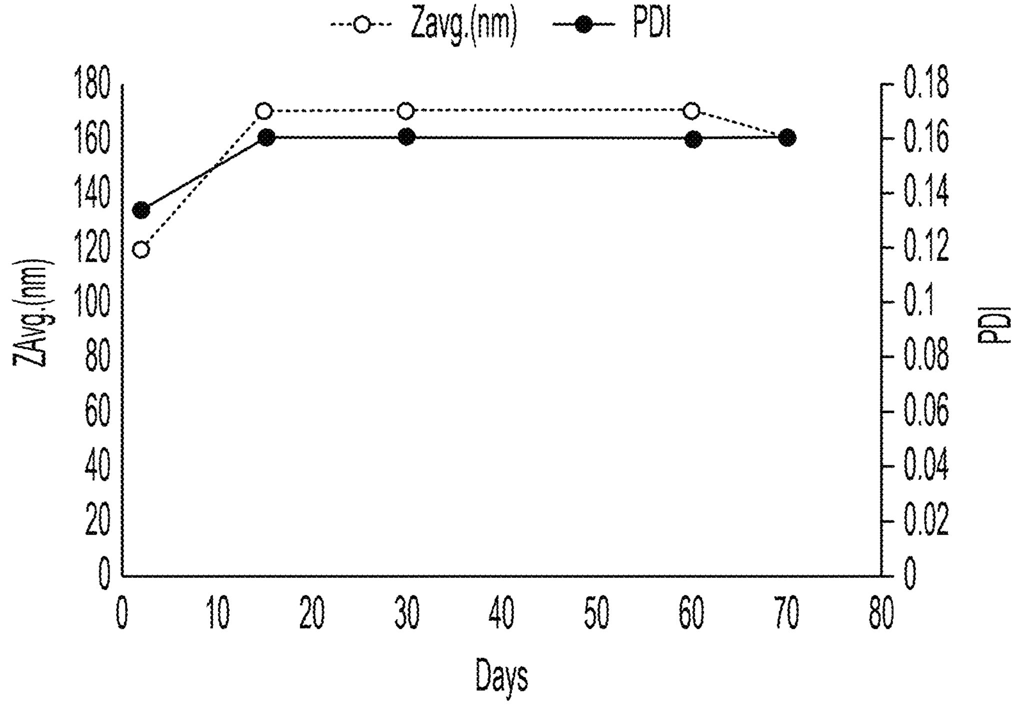

FIG. 13: The variation of the hydrodynamic size ($Z_{avg}$) of GNP-modified picolinium NPs by DLS over 70 days.

Examples of Polymersomes According to the Invention (Therafter Abbreviated Ps)

1. Chemical synthesis: preparation of picolinium and quinolinium derived redox probes, their incorporation as linkers between the two blocks of the block-copolymers Representative synthetic pathways are depicted in the schemes 1-4 below for representative compounds of formula (I) of the invention:

Scheme 2. Synthesis of PBLG$_n$-N$_3$

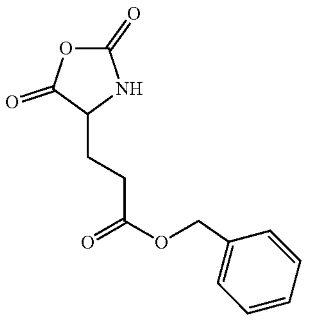

Benzyl-L-glutamate N-carboxyanhydride (BLG-NCA)

+

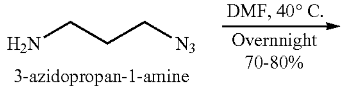

3-azidopropan-1-amine

Scheme 1. Synthesis of alkylated picolinium PEG esters (Pico-PEGs)

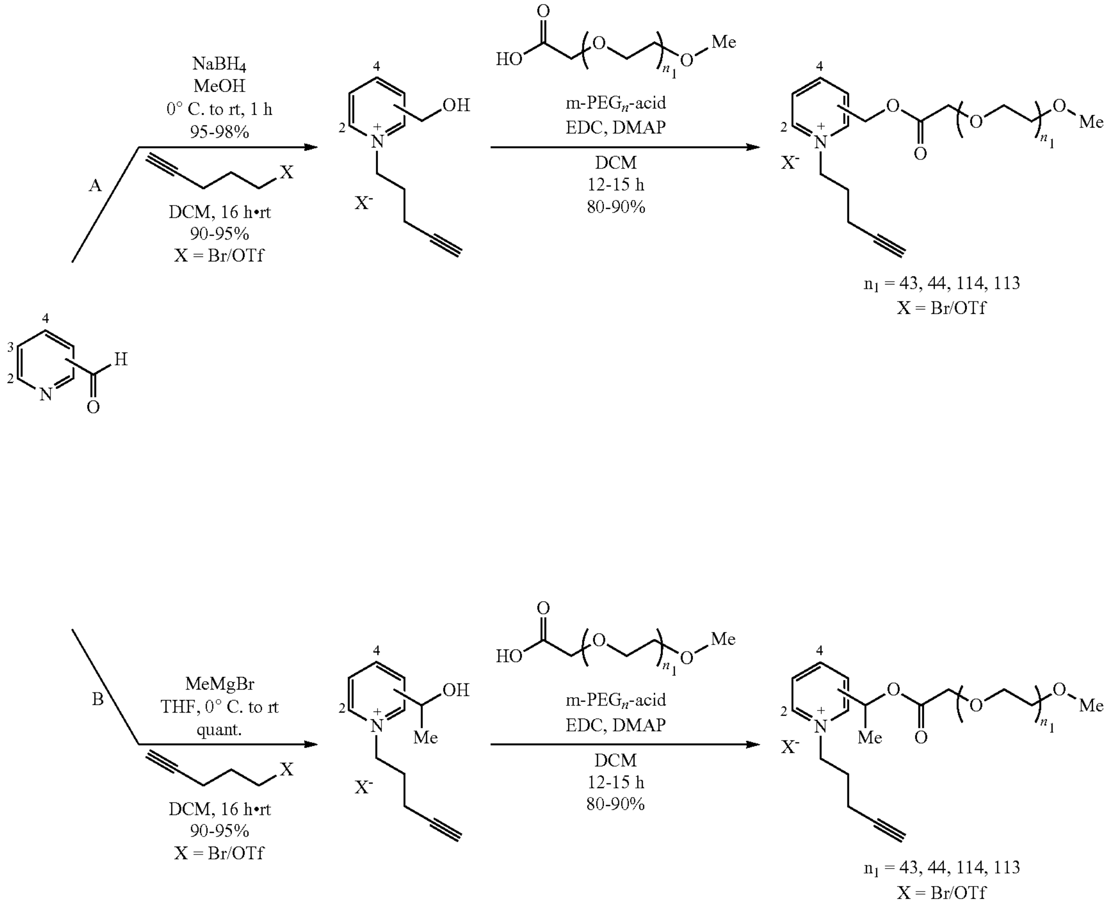

-continued
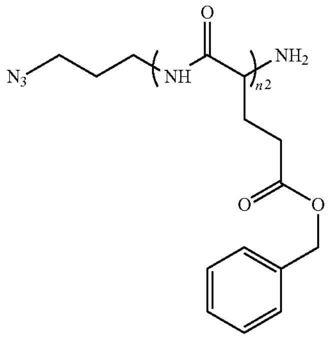
Azido-PBLG$_{n2}$
Where n2 = 17, 19, 20, 21, 24, 26, 29
Scheme 3. Preparation of block copolymers
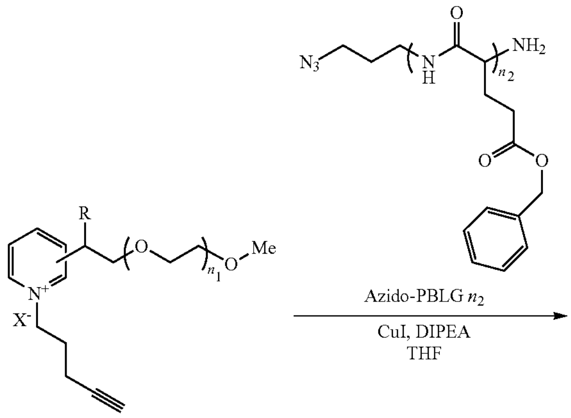
-continued
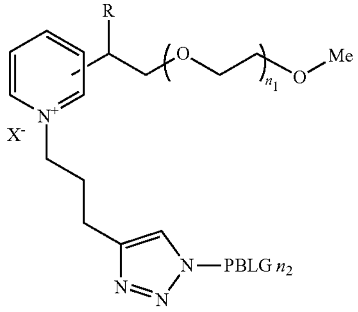
Block co-polymers
(NB: $n_1$ and $n_2$ as used in Schemes 1-3 corresponds to $n_2$ and $n_4$ respectively in Formula (I)).

Scheme 4. Synthesis of quinolinium-derived block copolymers (NB: n as used in Scheme 4 corresponds to n4 in Formula (I))
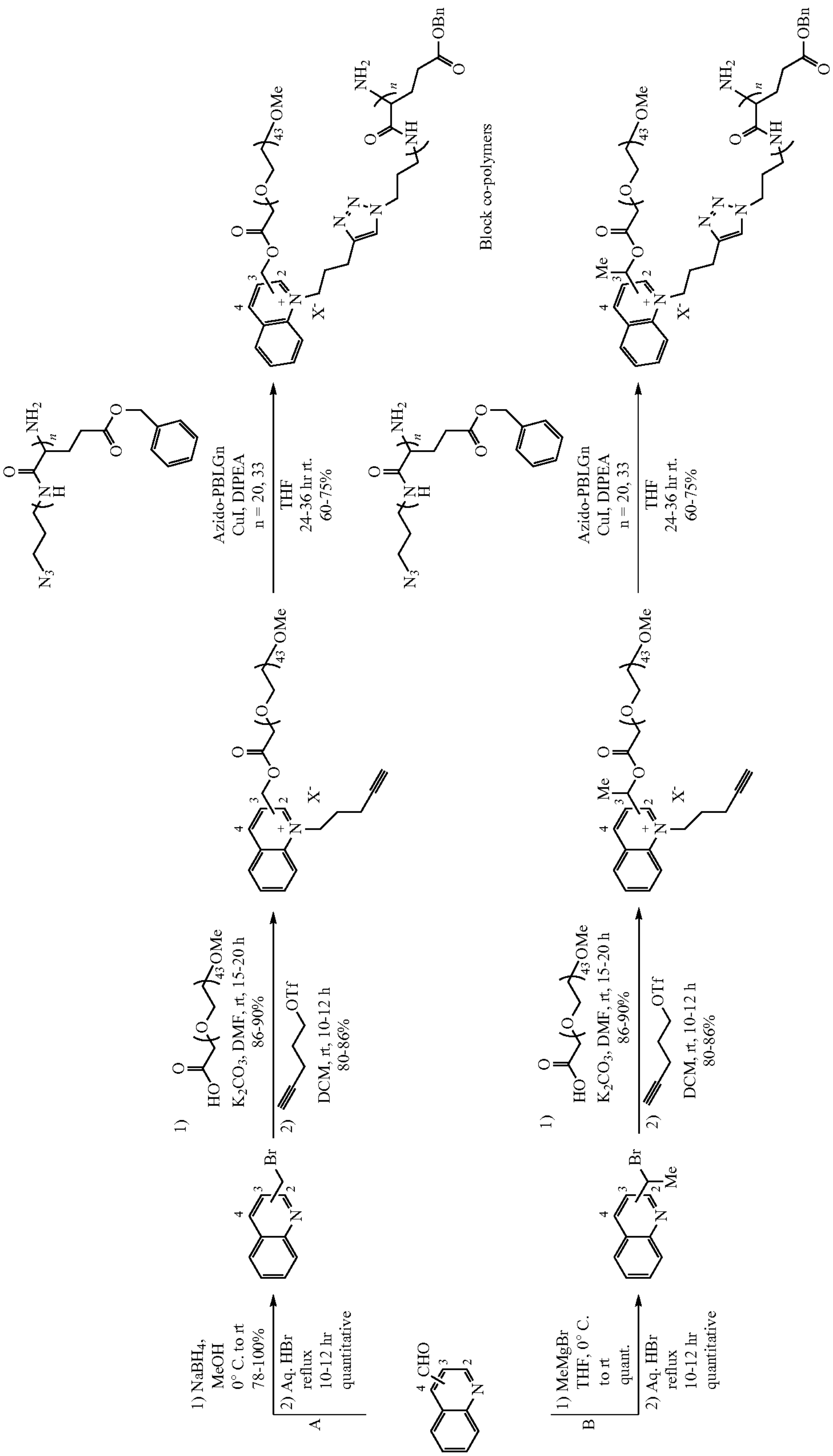

Generals

Proton nuclear magnetic resonance ($^1H$ NMR) spectra and carbon nuclear magnetic resonance ($^{13}C$ NMR) spectra were recorded on a Bruker 250 spectrometer (250 MHz and 63 MHz) and on a Bruker AV-500 spectrometer (500 MHz and 125 MHz). Chemical shifts for protons are reported in parts per million (ppm) downfield from tetramethylsilane (TMS) and are referenced to residual proton in the NMR solvent ($CDCl_3$: δ 7.26). Chemical shifts for carbon are reported in parts per million downfield from tetramethylsilane and are referenced to the carbon resonances of the solvent $CDCl_3$ (δ 77.16). NMR spectra recorded in other solvent are indicated in the experimental part.

Data are represented as follows: chemical shift, integration, multiplicity, coupling constants in Hertz (Hz). The following abbreviations are used to set multiplicities: s=singlet, bs=broad singlet, d=doublet, dd=double doublet, ddd=double double doublet, t=triplet, m=multiplet, br m=broad multiplet, bb=broad band.

All solvents and inorganic reagents were from commercial sources and used without purification unless otherwise noted. Thin layer chromatography (TLC) was performed on aluminium-backed plates, in particular MERCK® Kieselgel 60 F254 precoated plates. The high-performance liquid chromatography (HPLC) analyses were carried out on WATERS® device 600 with a normal inverse phase column XTERRA XTerra® MS C18 (length: 75 mm, diameter: 4.6 mm, stationary phase: 2.5 μm) using a Waters® 2487 Dual Absorbance Detector (254-365 nm) and an isocratic/linear gradient system of elution (Methanol-ACN-$H_2O$ 7-2-1/$H_2O$—$AcONH_4$ 10 mM pH 4.6). The volume of injection was 10 μL. The mass analyser was an AGILENT® from THERMOFISHER®. The capillary tension was 3.5 kV. The cone tension was 24 V. The temperature of the source was 130° C. and the temperature of desolvatation was 350° C. Data were treated on THERMOQUEST® data handling device.

Synthesis of N-Methyl Picolinium Esters

General Procedure for the Synthesis of Picoline Methyl-Alcohols

To a solution of the corresponding pyridine carboxaldehydes (3 mmol) in methanol at 0° C. was added sodium borohydride (1.2 eq.). The mixture was stirred at room temperature (RT) for 1 h before being quenched with HCl (1 M). The solution was then filtered on celite, washed with DCM and concentrated under reduced pressure. The crude product was purified by column chromatography on silica gel (DCM/MeOH 9/1) to obtain the corresponding alcohol.

Pyridin-2-ylmethanol

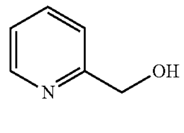

Yellow oil (320 mg, 98%).

Chemical formula: $C_6H_7NO$ Molecular Weight: 109.12 $g{\cdot}mol^{-1}$ $^1H$ NMR ($CDCl_3$, 250 MHz): δ 8.88-8.54 (1H, m), 7.69 (1H, m), 7.29-7.18 (2H, m), 4.75 (2H, s), 3.16 (1H, bs,).

$^{13}C$ NMR ($CDCl_3$, 250 MHz): δ 159.6, 148.4, 136.9, 122.3, 120.8, 64.3.

MS (ESI): m/z=110.0 $[M+H]^+$.

Preparation of 5-bromopent-1-yne

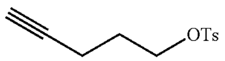 [SMILES: C#CCCCOS(=O)(=O)c1ccc(C)cc1]

Pent-4-yn-1-yl 4-methylbenzenesulfonate 29: In a solution of pent-4-yn-1-ol (1 eq.) in DCM (10 v), was added triethylamine (2.0 eq) and the solution stirred at 0-5° C. for 10 minute, followed by the addition of tosyl chloride (1.2 eq.) at this temperature. The reaction was left to stir for 10 to 15 h at room temperature. The progress was monitored by TLC in EtOAc/cyclohexane (20:80). The reaction was quenched by the addition of water (20 mL) and the product extracted with DCM 2 to 3 times, dried over $Na_2SO_4$, filtered and concentrated in vacuo. Solid mass obtained (off white; 95%).

$^1H$ NMR ($CDCl_3$, 250 MHz): δ 7.82 (d, 2H), 7.38 (d, 2H), 4.18 (t, 2H), 2.46 (s, 3H), 4.77-4.74 (t, 2H), 2.47 (s, 1H), 2.30-2.24 (dd, 2H), 1.91-1.89 (t, 1H), 1.88-1.82 (q, 2H).

5-Bromopent-1-yne

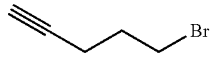

To a solution of pent-4-yn-1-yl 4-methylbenzenesulfonate (1.0 eq.) in DMSO (8 v) was added LiBr (5.0 eq) (exothermicity observed). The reaction was stirred overnight at room temperature. The reaction was quenched by the addition of water (100 mL), followed by stirring for 10 minutes. The product was extracted using DCM 2 to 3 times, dried over $Na_2SO_4$, filtered and concentrated in vacuo. Oily mass obtained (colorless; 72% yield).

$^1H$ NMR ($CDCl_3$, 250 MHz): 3.59-3.53 (t, 2H), 2.45-2.39 (dd, 2H), 2.13-2.05 (q, 2H), 2.03-2.00 (t, 1H).

Preparation of pent-4-yn-1-yl trifluoromethanesulfonate

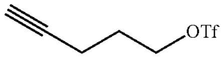

To a solution of pent-4-yn-1-ol (1 eq.) in DCM (10 v), was added pyridine (1.2 eq.) and stirred at 0-5° C. for 5 minutes under inert atm., followed by the addition of triflic anhydride (1.2 eq) at the same temperature. The reaction was stirred for 2 h at room temperature. The reaction was quenched by the addition of water (5 mL) and the product extracted with DCM 2 to 3 times, dried over $Na_2SO_4$, filtered and concentrated in vacuo. Light brown semi solid 81%).

$^1H$ NMR ($CDCl_3$, 250 MHz): 4.62-4.56 (t, 2H), 2.78-2.72 (dd, 2H), 2.30-2.24 (dd, 2H), 2.18-2.12 (m, 3H).

Quaternarization of Various Hydroxymethyl Picolines 2-(Hydroxymethyl)-1-(pent-4-yn-1-yl) pyridin-1-ium

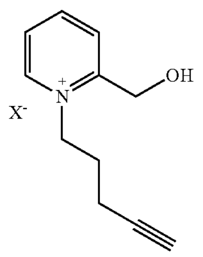

To a solution of hydroxymethyl picoline (500 mg, 1.00 eq.) in ACN (3 mL), pent-4-yn-1-yl triflate (936 mg, 1.4 equiv.) was added and the solution was stirred at 60-70° C., overnight. Solvent was concentrated in vacuo at 40° C. and the crude product was purified by column chromatography using silica gel (DCM: MeOH). Light brown semi solid, 91%.

Chemical Formula: $C_{11}H_{14}NO^{+}$ Molecular Weight: 176.24 g·mol$^{-1}$ $^{1}$H NMR (MeOD, 500 MHz): δ 8.90 (d, J=6.3 Hz, 1H), 8.56 (td, J=7.9, 1.5 Hz, 1H), 8.25-(d, J=8.4 Hz, 1H), 7.98 (ddd, J=7.7, 6.2, 1.6 Hz, 1H), 5.03 (s, 2H), 4.68-4.65 (m, 2H), 2.40-2.37 (m, 3H), 2.20-2.14 (m, 2H).

General Method for the Synthesis of Azido Poly(γ-Benzyl-L-Glutamate)

Synthesis of PBLG$_{21}$-N$_3$

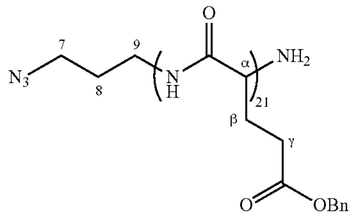

In a glove-box, γ-benzyl-L-glutamate N-carboxyanhydride (BLG-NCA) (2 g, 7.6 mmol) was dissolved in dry DMF (20 mL). The flask was maintained under argon and brought to the fume-hood, where 1-azido-3-aminopropane (36 μL, 0.362 mmol) was added under argon. The reaction mixture was stirred for 18 h at 40° C. The polymer was precipitated by slowly adding the reaction mixture into cold $Et_2O$ (200 mL). The precipitate was filtered, washed with cold $Et_2O$, and dried in vacuo to provide PBLG$_{21}$-N$_3$ (1.44 g, 86% yield) as a white powder.

$^{1}$H NMR (90/10 $CDC_3$/TFA, 400 MHz): δ 7.98-7.80 (m, 21H, amide-NH), 7.41-7.22 (m, 105H, aromatic-CH), 5.17-5.05-(m, 42H, Bz-$CH_2$), 4.65-4.55 (m, 21H, α-CH), 3.40-3.35 (m, 4H, 7-$CH_2$, 9-$CH_2$), 2.58-2.39 (m, 42H, γ-$CH_2$), 2.22-2.04 (m, 21H, β-$CHH_2$), 2.00-1.86 (m, 21H, β-CHH), 1.82-1.77 (m, 2H, 8-$CH_2$).

SEC: Đ=1.13.

Synthesis of PBLG-N$_3$ of Different DPs (PBLG$_{20}$-N$_3$, PBLG$_{21}$-N$_3$, PBLG$_{26}$-N$_3$ and PBLG$_{33}$-N$_3$)

Ring opening polymerization (ROP) of γ-benzyl-L-glutamate N-carboxyanhydride was performed using a 1-azido-3-aminopropane as an initiator to afford α-azido poly(γ-benzyl-L-glutamate) (PBLG) (Scheme 5). Initiator 1-azido-3-aminopropane was synthesized as previously reported (Agut et al, *Macromol. Rapid Commun.* 2008, 29, 1147-1155). PBLG-N$_3$ polymers of different degrees of polymerization (DPs) were synthesized by ROP in DMF, the reaction being carried for 18 h out at 40° C. For example, for PBLG$_{21}$-N$_3$, γ-benzyl-L-glutamate N-carboxyanhydride (BLG-NCA) (2 g, 7.6 mmol) was dissolved in dry DMF (20 mL) inside a glove-box to protect the NCA from moisture. The flask was maintained under argon and brought to the fume-hood, where 1-azido-3-aminopropane (36 μL, 0.362 mmol) was added under argon. The reaction mixture was stirred for 18 h at 40° C. The polymer was precipitated by slowly adding the reaction mixture into cold $Et_2O$ (200 mL). The precipitate was filtered, washed with cold $Et_2O$, and dried in vacuo to provide PBLG$_{21}$-N$_3$ (1.44 g, 86% yield) as a white powder.

$^{1}$H NMR (90/10 $CDC_3$/TFA, 400 MHz): δ 7.98-7.80 (m, 21H, amide-NH), 7.41-7.22 (m, 105H, aromatic-CH), 5.17-5.05-(m, 42H, Bz-$CH_2$), 4.65-4.55 (m, 21H, α-CH), 3.40-3.35 (m, 4H, 7-$CH_2$, 9-$CH_2$), 2.58-2.39 (m, 42H, γ-$CH_2$), 2.22-2.04 (m, 21H, β-CHH), 2.00-1.86 (m, 21H, β-CHH), 1.82-1.77 (m, 2H, 8-$CH_2$). SEC: Đ=1.13. Different DPs were obtained by varying the ratio of monomer to initiator. This provided PBLG$_{20}$-N$_3$, PBLG$_{21}$-N$_3$, PBLG$_{26}$-N$_3$, and PBLG$_{33}$-N$_3$ (Table A). The DPs were determined by $^{1}$H NMR spectroscopy in 90:10 $CDC_3$:trifluoroacetic acid (TFA), based on the integrations of the peaks at ~3.35 ppm and ~4.59 ppm, where the peak at ~3.35 was integrated to 4 as it corresponds to the methylene groups α—to the amide and azide of the initiator, and the peak at ~4.59 corresponds to the α-carbon of benzyl glutamate. Size exclusion chromatography (SEC) in DMF was used to obtain the molar mass dispersity (Đ) of 1.05-1.13. SEC chromatograms exhibited a bimodal distribution: Such bimodality for polypeptide chains is usually observed and ascribed to coexistence of helical and random coil structures in solution (Lecommandoux et al, *Macromol.* 2001, 34, 9100-9111; Huesmann et al *Macromol.* 2014, 47, 928-936), thus PBLG likely undergoes similar conformational equilibrium, explaining bimodality in SEC.

Scheme 5 Synthesis of PBLG-N$_3$

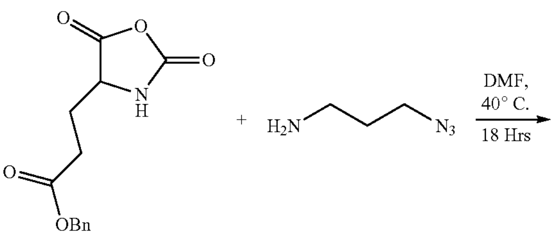

-continued

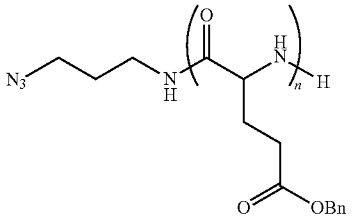

TABLE A

| PBLG-N3 | | | | |
|---|---|---|---|---|
| Entry | $PBLG_n$-$N_3$ | DP[a] | Mn (g/mol)[a] | Đ[b] |
| 1 | $PBLG_{20}$-$N_3$ | 20 | 4485 | 1.05 |
| 2 | $PBLG_{21}$-$N_3$ | 21 | 4704 | 1.13 |
| 3 | $PBLG_{26}$-$N_3$ | 26 | 5800 | 1.10 |
| 4 | $PBLG_{33}$-$N_3$ | 33 | 7333 | 1.10 |

([a]determined by NMR, [b]determined by SEC)

MeO-$PEG_{43}$-COOH

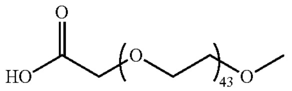

Polyethylene glycol monomethyl ether (2 kg·mol$^{-1}$) (5 g, 2.5 mmol), TEMPO (2 mg, 0.125 mmol) and KBr (30 mg, 0.25 mmol) were dissolved in 60 mL of DI $H_2O$. An 8% sodium hypochlorite solution (3 mmol sodium hypochlorite/mmol primary alcohol) was added, the pH of the reaction mixture was adjusted to pH ~10 and the reaction left to stir for 18 h. TLC showed 50% completion. EtOH (5 mL) was added and the pH reduced to pH ~3, the mixture of product and starting material was extracted with DCM (×5) dried over $MgSO_4$, filtered, concentrated in vacuo and precipitated in $Et_2O$.

The precipitate was subjected to the above procedure with the same quantities of TEMPO, KBr, NaOCl and $H_2O$. The reaction was left for 48 h, TLC showed no starting material. EtOH (5 mL) was added and the pH reduced to pH ~3, extracted with DCM (×5) dried over $MgSO_4$, filtered, concentrated in vacuo and precipitated in $Et_2O$ to give the product MeO-$PEG_{43}$-COOH (4.3 g, 86%).

$^1$H-NMR ($CDCl_3$, 400 MHz): δ 4.15 (s, 2H, CHr-COOH), 3.76-3.73 (m, 2H, PEG-$CH_2$), 3.69-3.62 (m, 168H, PEG-$C_2H_4$), 3.55-3.53 (m, 2H, PEG-$CH_2$), 3.37 (s, 3H, $CH_3O$).

General Method for the Synthesis of Pico-PEG

MeO-PEG-COOH (1.15 eq.) and linker (1 eq.) were dissolved dry DCM. EDC-HCl (2 eq) and DMAP (0.2 eq) were dissolved DCM and this was added to the reaction mixture and left to stir for 48 h. The reaction mixture was then precipitated in $Et_2O$, the precipitate was dried, re-dissolved in DCM and washed with brine. The product was extracted from brine with DCM (×5), dried over $MgSO_4$, filtered, concentrated in vacuo, dissolved in minimum acetone and precipitated in $Et_2O$ to give the product Pico-PEG (79%-99%).

Pico-PEG

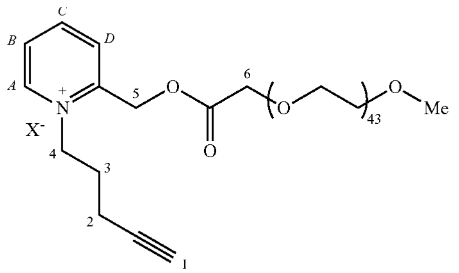

MeO-$PEG_{43}$-COOH (512 mg, 0.2604 mmol) and picolinium linker (58 mg, 0.2264 mmol) were dissolved 8 mL dry DCM. EDC.HCl (87 mg, 0.453 mmol) and DMAP (6 mg, 0.0453 mmol) were dissolved 2 mL dry DCM. (454 mg, 92%).

$^1$H-NMR ($CDCl_3$, 400 MHz): δ 10.25 (dd, J=6.7, 1.1 Hz, 1H, A-aromatic CH), 8.49 (td, J=7.9, 1.1 Hz, 1H, C—CH), 8.13-8.09 (m, 2H, B—CH, D-CH), 5.73 (s, 2H, 5-$CH_2$), 5.21 (t, J=7.7 Hz, 2H, 4-$CH_2$), 4.33 (s, 2H, 6-$CH_2$), 3.76-3.73 (m, 2H, PEG-$CH_2$), 3.60-3.70 (m, 168H, PEG-$C_2H_4$), 3.55-3.53 (m, 2H, PEG-$CH_2$), 3.37 (s, 3H, $OCH_3$), 2.52 (td, J=6.4, 2.6 Hz, 2H, 2-$CH_2$), 2.35-2.31 (m, 2H, 3-$CH_2$), 2.06 (t, J=2.6 Hz, 1H, 1-H).

Block Copolymer $PEG_{43}$-Pico-b-$PBLG_{21}$

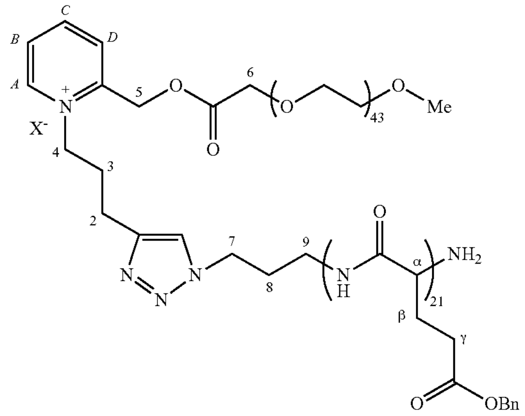

Pent-4-yn-1-yl picolinium triflate (232 mg, 0.1063 mmol) and PBLG-$N_3$ (200 mg, 42.5 μmol) were dissolved in dry THF (7 mL). CuI (8 mg, 42.5 μmol) and DIPEA (15 μL, 85 μmol) were added sequentially and the reaction mixture was left to stir under argon for 18 h. The reaction mixture was concentrated and purified by silica gel column chromatography (MeOH: DCM, v:v, 1:50→3:20). The product was re-dissolved in minimum DCM and precipitated in $Et_2O$. The precipitate was dried in vacuo to give the product (210 mg, 71%).

$^1$H-NMR ($CDCl_3$, 400 MHz;): δ 8.35-8.17 (m, 19H, amide-NH). 7.34-7.16 (m, 105H, Bz-aromatic-CH), 5.14-4.95 (m, 46H, Bz-$CH_2$, 4-$CH_2$, 5—$CH_2$), 3.98-3.80 (m, 23H, α-CH, 6-$CH_2$), 3.79-3.46 (m, 174H, PEG-$C_2H_4$, 7—$CH_2$), 3.38 (s, 3H, $OCH_3$), 3.31-3.35 (m, 2H, 9-$CH_2$), 2.79-2.01 (broad m, 88H, 2-$CH_2$, 3—$CH_2$, R—$CH_2$, γ-$CH_2$), 1.86-1.82 (m, 2H, 8-$CH_2$).

SEC: Đ=1.09.

Synthesis of N-methyl Quinolinium Esters

General Procedure for the Synthesis of Quinoline Aldehydes

The appropriate quinoline (1.0 eq.) was introduced to a suspension of selenium dioxide (1.3 eq.) in dioxane, and the mixture was heated at 80° C. for 3 h. After cooling the mixture to rt, the solid was filtered on celite, washed with EtOAc and concentrated under reduced pressure. The crude product was purified by column chromatography on silica gel (Cyclohexane/EtOAc: 4/1) to obtain the corresponding aldehyde as an orange-red solid.

Quinoline-2-carbaldehyde

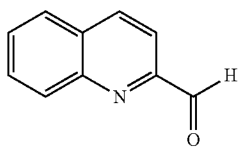 [SMILES: O=Cc1ccc2ccccc2n1]

Following general procedure, 2 g (13.96 mmol) of quinaldine was reacted with 2.013 g (18.14 mmol) of selenium dioxide to obtain quinoline-2-carbaldehyde (2.01 g, 92%) Chemical formula: $C_{10}H_7NO$ Molecular Weight: 157.17 $g \cdot mol^{-1}$ $^1H$ NMR ($CDCl_3$, 500 MHz): δ 10.24 (s, 1H), 8.32 (d, J=8.5 Hz, 1H), 8.26 (d, J=8.5 Hz, $^1H$), 8.04 (d, J=8.5 Hz, 1H), 7.91 (d, J=8 Hz, 1H), 7.83 (t, J=10 Hz, 1H), 7.70 (t, J=7 Hz, 1H).

$^{13}C$ NMR ($CDCl_3$, 125 MHz): δ 193.9, 152.8, 148.1, 137.5, 130.63, 130.6, 130.2, 129.4, 128.0, 117.5.

MS (ESI): m/z=158.1 $[M+H]^+$, 189.9 (hemiacetal).

General Procedure for the Synthesis of Quinoline Methyl-Alcohols

To a solution of the corresponding aldehydes (1.0 eq.) in methanol at 0° C. was added sodium borohydride (1.2 eq.). The mixture was stirred at rt for 1 h before being quenched with HCl 1M. Water was added and the product was extracted with DCM. The organic layer was washed twice with water and brine, dried over $MgSO_4$, filtered and concentrated under reduced pressure. The product obtained was used without further purification.

Quinolin-2-ylmethanol

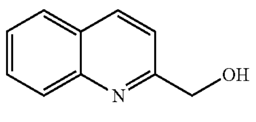 [SMILES: OCc1ccc2ccccc2n1]

Following general procedure, 0.8 g (5.08 mmol) of quinolone carbaldehyde was reacted with 0.230 g (6.1 mmol) of sodium borohydride to obtain quinolin-2-ylmethanol (0.77 g, 95%).

Chemical formula: $C_{10}H_9NO$ Molecular Weight: 159.19 $g \cdot mol^{-1}$ $^1H$ NMR ($CDCl_3$, 500 MHz): δ 8.14 (d, J=8.5 Hz, 1H), 8.08 (d, J=8.5 Hz, 1H), 7.82 (d, J=8 Hz, 1H), 7.73 (m, 1H), 7.54 (m, 1H), 7.28 (d, J=8.5 Hz, 1H), 4.92 (s, 2H). $^{13}C$ NMR ($CDCl_3$, 125M Hz): δ 159.1, 146.9, 137.0, 130.0, 128.8, 127.83, 127.80, 126.5, 118.5, 64.3.

General Procedure for the Synthesis of Brominated Quinolines

Aqueous HBr (49%) (10 mL) was directly poured into appropriate quinoline alcohols, and the mixture was heated up to reflux for 10-12 h. Solvents were evaporated under reduced pressure and the crude was dried under vacuum in the presence of $P_2O_5$ to remove trace of water; Brown solid.

2-(Bromomethyl) quinoline hydrogen bromide

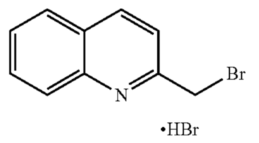 [SMILES: BrCc1ccc2ccccc2n1 ; Br]

Following general procedure, 10 mL of aqueous hydrogen bromide was added to 1.0 g (6.0 mmol) of alcohol to obtain the desired halogenated compound (1.9 g, quant.).

Chemical Formula: $C_{10}H_8BrN$ Molecular Weight: 222.09 $g \cdot mol^{-1}$ $^1H$ NMR ($(CD_3)_2SO$, 500 MHz): δ: 9.18 (d, J=8.27 Hz, 1H), 8.84 (d, J=8.8 Hz, 1H), 8.26 (d, J=10.2 Hz, 1H), 8.04 (d, J=8.7 Hz, 1H), 7.85 (dd, J=8.0, 1.6 Hz, 1H), 7.77 (m, 1H) 5.12 (s, 1H).

$^{13}C$ NMR ($(CD_3)_2SO$, 500 MHz): δ 161.1, 159.5, 146.3, 138.8, 134.6, 132.5, 128.1, 127.5, 127.1, 67.1.

General Procedure for Quinolinium PEG Esters

The brominated quinoline (1.2 eq.) was dissolved into DMF in the presence of $K_2CO_3$ (2.5 eq.), MeO-$PEG_{43}$-COOH (1.0 eq.) was introduced into this solution & mixture was heated at 40° C. for 24-32 h. After cooling the mixture to rt, brine solution was added to the reaction mixture washed with EtOAc (2 to 3 times) and concentrated under reduced pressure. The oily mass was further precipitated by diethyl ether to obtain the corresponding off-white solid.

Quinoline 2-hydroxymethylene PEG Ester

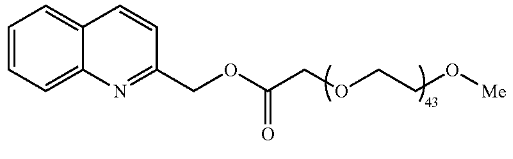

Following the general procedure, 2.0 g (1 mmol) of MeO-$PEG_{43}$-COOH was reacted with the bromo-compound (0.290 g, 1.3 mmol) in the presence of 0.414 g $K_2CO_3$ (3 mmol) to obtain the desired ester (1.7 g, 85%).

$^1H$ NMR ($CDCl_3$, 500 MHz): δ 8.22 (d, J=8.2 Hz 1H), 8.09 (d, J=8.2 Hz 1H), 7.85 (d, J=8.5 Hz 1H), 7.76-7.71 (dd,

J=9.4, 6.5 Hz 1H), 7.60-7.54 (t, J=8.24 Hz 1H), 7.5-7.48 (d, J=8.5 Hz 1H), 5.49 (s, 2H), 4.33 (s, 2H), 3.66 (s, 121H, —$CH_3$ $mPEG_{2000}$), 3.39 (s, 3H, —$OCH_3$ $mPEG_{2000}$). $^{13}C$ NMR ($CDCl_3$, 500 MHz): δ 174.4, 170.2, 155.6, 147.6, 137, 129.9, 129.2, 127.6, 126.7, 119.5, 71.9, 70.6 (m-PEG-$CH_2$), 69.7, 67.5, 59.

General Procedure for Preparation of Block Co-Polymers

Quinoline-PEG esters (1 eq) and pent-4-yn-1-yl trifluoromethanesulfonate (1.2 eq) were dissolved in DCM and stirred at room temperature for 72 h. The mixture was evaporated after that these products used in situ as for preparation of block co polymers. Block copolymers were synthesized. Alkyne derivatives (1 eq.) and PBLG-$N_3$ (2.5) were dissolved, respectively, in dry THF (7 mL). Cul (1 eq.) and DIPEA (2 eq.) were added sequentially and the reaction mixture was left to stir under argon for 24-36 h. The reaction mixture was concentrated and redissolved in DCM, this solution was washed by aqueous solution of EDTA (10%) at least two times. The organic solution was dried over $Na_2SO_4$ and concentrated the mass under vacuum. The desired product was precipitated in diethyl ether. Off-white semi solid mass was obtained (60-75%).

Block Co-Polymer (Quino)

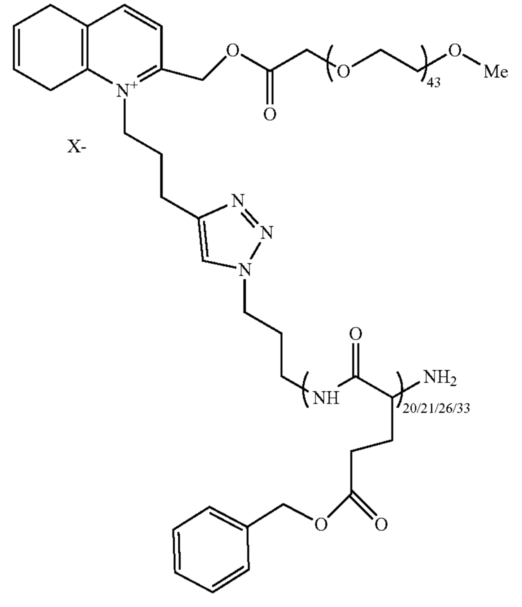

100 (130 mg, 55 μmol) and $PBLG_{20}$-$N_3$/$PBLG_{21}$-$N_3$ (100 mg, 22 μmol) were dissolved in dry THF (3.5 mL). Cul (8.3 mg, 4 μmol) and DIPEA (4.2 μL, 5 μmol) were added sequentially and the reaction mixture was left to stir under argon for 24-36 h. Semi-solid off-white color 97.5 mg (75/72%) compounds obtained respectively.

$^1H$ NMR ($CDCl_3$ 500 MHz): δ

Hydrophobically Coated Very Small Iron Oxide Nanoparticles (VSION)

Very small iron oxide NPs (VSIONs) of diameters around 4 nm were synthesized by the polyol route with slight modifications to control the nucleation-growth process through the water content of the solvent mixture, as reported in Hemery et al *Inorganic Chemistry,* 2017, 56(14), 8232-8243. Namely 1.082 g (4 mmol) of $FeCl_3.6H_2O$ and 0.398 g (2 mmol) of $FeCl_2$-$4H_2O$ were dissolved in 80 g of diethylene glycol (DEG). Separately, 0.64 g (16 mmol) of NaOH pearls was dissolved in 40 g of DEG. Both solutions were stirred overnight under nitrogen flux to prevent oxidation of the Fe(II) species. The solutions were then mixed and stirred for 3 h, before heating the mixture at 210° C. with an oil bath, reflux set-up and mechanical agitation. At first the set-up was open and a flux of nitrogen helped to remove traces of water. When a temperature of 210° C. was reached the set-up was closed, and hot injection of 2.5 mL water (137 mmol) in the vessel through a septum led to a burst of nuclei. The formation of nanoparticles through forced hydrolysis pathway was carried out for 30 min, before letting the system cool down to RT by removing the heating plate. The black sediment was separated magnetically and washed 3× with a mixture of EtOH and EtOAc (1:1 v/v). Possibly present non-magnetic iron oxohydroxides were removed by treatment with 10% nitric acid. 8.6 g of $Fe(NO_3)_3.9H_2O$ was then added to the solution as a strong oxidant by heating at 80° C. for 45 min while mechanically stirring. The solution then turned from clear black (magnetite $Fe_3O_4$) to red (maghemite γ-$Fe_2O_3$). The IONPs were then washed 2 times with acetone and 2 times with $Et_2O$ before being dispersed in water. The morphology of nanoparticles was investigated by TEM and automated particle sizing led to a diameter range of 4.3±1.1 nm.

The commercial dispersing agent Beycostat™ NE (NB09, CECA, Puteaux, France) was used to coat the surface of the VSIONs and render them hydrophobic. This surfactant is a mixture of mono- and di-esters of phosphoric acid with poly(ethylene oxide)$_9$ nonylphenyl ether chains. To a mixture of 2.55 mL acidic aqueous VSION dispersion at 18.0 g/L iron oxide (45 mg solid content) and 235 mg of BNE (liquid), 6.5 mL of a 2 M $HNO_3$ solution was added and the reaction stirred vigorously (400 rpm) with a mechanical stirrer at 60° C. for ~15 minutes. The VSIONs were settled over a permanent magnet and the supernatant pipetted out. The BNE-coated VSIONs were washed 5× with 10 mL MeOH, before being dispersed in 2.5 mL of THF. The iron oxide content of this dispersion was estimated by dissolving 50 μL of suspension in 5 mL of HCl 5M with help of a sonication bath. The absorbance (optical density) at 350 nm was converted through predetermined calibration, $OD_{350\ nm,\ 2\ mm}$=0.5043×$[Fe]_{mM}$+0.0172, into a concentration of 0.91 g/L γ-$Fe_2O_3$ in THF. DLS measurement with multi-modal (CONTIN) analysis showed peaks at 7.5 and 37.5 nm.

2. Self-Assembly Process

Preparation of Self-Assembled Structures for Morphology Studies

Nanoprecipitations of Picolinium Block Co Polymers:

Block copolymer $PEG_{44}$-Pico-b-$PBLG_{17}$: 900 μL of water was added fast (in one shot) to a solution (100 μL) of block co-polymer (1 mg) in DMSO. This was dialyzed (3.5 kDa cutoff membrane) against ultrapure water for 18 h. DLS measurement led to Z-Avg=93 nm, PDI=0.17. Micelle morphology was observed by TEM.

Here Z-Avg represented Z-averaged diameters (2 times $R_h$) determined by a $2^{nd}$ order Cumulant fit of the DLS curves.

Block copolymer $PEG_{43}$-Picol-b-$PBLG_{21}$: 4.5 mL of water was added fast (in one shot) to a solution (500 μL) of block copolymer Pico (5 mg) in THF. It was dialyzed (3.5 kDa cutoff membrane) against ultrapure water for 18 h. DLS measurement led to Z-Avg=143 nm, PDI=0.105. Polymersomes where formed, as evidenced by MALS (ALV ρ-ratio=1.1), TEM and Cryo-TEM images.

2.67 mL of water was added quickly to a solution (330 μL) of block copolymer Pico (3.3 mg) in DMSO. The suspension was dialyzed (3.5 kDa) against ultrapure water for 18 h. DLS measurement led to Z-Avg=293 nm, PDI=0.261. Micelles were analyzed by TEM.

Nanoprecipitation with saline solution 2.7 mL of 0.9% aq. NaCl was added quickly to a solution (300 μL) of block copolymer Pico (3 mg) in THF. The suspension was dialyzed (3.5 kDa cutoff membrane) against 0.9% aq. NaCl for 18 h. Z-Avg=120 nm, PDI=0.118. Polymersomes were analyzed by TEM and MALS (ALV ρ-ratio=1.2).

Nanoprecipitation with hydrophobic v-$Fe_2O_3$ VSIONs A suspension (6.6 μL, 5% FWR relatively to polymer) of Beycostat coated 4.3±1.1 nm diameter γ-$Fe_2O_3$ VSIONs was added to a solution (200 μL) of block copolymer Pico (2 mg) in THF and nanoprecipitation occurred by fast addition of water (1.7 mL). This suspension was kept into a semi-permeable membrane tube (3.5 kDa cutoff) & dialyzed against ultrapure water for 18 h. The nanoparticles were analyzed by DLS: Z-Avg=129 nm, PDI=0.273. Polymersome morphology with iron oxide nanoparticles buried in the hydrophobic membranes were observed by TEM and cryo-TEM.

Nanoprecipitation with hydrophobic v-$Fe_2O_3$ NPs in saline solution A suspension (15 μL, 10% FWR relatively to polymer) of Beycostat coated 4.3±1.1 nm diameter γ-$Fe_2O_3$ VSIONs was added to a solution (220 μL) of block copolymer Pico (2.2 mg) in THF, then 0.9% aq. NaCl (2 mL) solution was added fast into it. This suspension was dialyzed (3.5 kDa cutoff) against 0.9% aq. NaCl for 18 h. DLS analysis led to Z-Avg.=142 nm, PDI=0.201. Polymersome formation was ascertained by MALS (ALV ρ-ratio=1.0) and iron oxide nanoparticles buried in their hydrophobic membrane were observed by TEM.

Nanoprecipitations of Quinolinium Block Co Polymers:

Block copolymer Quino (1 mg) dissolved in THF (100 μL) and (900 μL) of 0.9% aq. NaCl was added promptly into it for nanoprecipitation. This solution was put in a dialysis bag (15 kDa cutoff) and dialyzed against 0.9% aq. NaCl for 24 h. DLS measurement led to Z-Avg=88 nm, PDI=0.10. TEM pictures suggested the formation of polymersomes. 900 μL DI water was added promptly into the solution of Block copolymer Qino (1 mg) in THF (100 μL) for nanoprecipitation. This solution was put in dialysis bag (15 kDa cutoff) and dialyzed against DI water for 18 h. Hydrodynamic size was measured by DLS: Z-Avg=73 nm, PDI=0.231.

Block copolymer Quino (1 mg/mL) dissolved in THF (100 μL) was added into (900 μL) DI water for nanoprecipitation. This solution was put in dialysis bag (15 kDa cutoff) and dialyzed against ultrapure water for 18 h. DLS measurement led to Z-Avg=59 nm, PDI=0.138. The TEM picture showed small vesicles that might rather be micelles, showing that the addition order is important (with Quino copolymer; vesicles are more likely formed when the aqueous solution is poured into organic polymer solution rather than with the reverse addition order).

Nanoprecipitation in saline Block copolymer Quino (1.5 mg) was dissolved in THF (100 μL) and (900 μL) of 0.9% aq. NaCl was added quickly into it for nanoprecipitation. This suspension was put in a dialysis bag (15 kDa cutoff) and was dialyzed against 0.9% aq. NaCl for 24 h. DLS measurement yielded a hydrodynamic diameter of Z-Avg=107 nm, PDI=0.130. The morphology was characteristic of polymersomes according to TEM and MALS (ALV ρ-ratio=1.0).

Nanoprecipitation with Hydrophobic v-$Fe_2O_3$ NPs in Saline

A suspension (23.4 μL, 5% FWR relatively to polymer) of Beycostat-coated 4.3±1.1 nm diameter γ-$Fe_2O_3$ VSIONs was added to a solution (100 μL) of block copolymer Quino (1.5 mg) in THF. Then 0.9% aq. NaCl (0.9 mL) was added quickly to the solution. The suspension was dialyzed (3.5 kDa cutoff) against saline for 18 h. Hydrodynamic diameter measured by DLS was Z-Avg=130 nm, PDI=0.120. Morphology according to TEM images consisted of polymersomes loaded with iron oxide NPs in their membrane.

Characterization

GPC

Gel permeation chromatography (GPC) also called size exclusion chromatography (SEC) was performed on an Ultimate 3000 system from Thermo Fisher scientific equipped with a differential refractive index detector (dRI) detector from Wyatt Technology corporation (Santa Barbara CA, USA), using DMF with LiBr (1 g/L) as the eluent at a flowrate of 0.8 mL/min. The column set consisted of two KD-803 Shodex™ gel columns (300×8 mm) (exclusion limits 1-50 kDa), maintained at 50° C. Weight-average molar massed ($M_W$) and mass dispersities (Đ) were calculated with ASTRA 7.1.0 software from the chromatograms calibrated using a series of polystyrene standards.

DLS

The hydrodynamic radii and size distribution of the self-assembled copolymers were measured at by dynamic light scattering (DLS) on a Zetasizer™, nano ZS instrument (Malvern company, UK) equipped with a 633 nm helium-neon laser using back-scattering detection at fixed 173° scattering angle on samples equilibrated at 25° C. The measured hydrodynamic sizes of the vesicles as well as the PDI values were obtained by the classical $2^{nd}$ order Cumulant fitting procedure of the scattered intensity correlograms (T=25° C., 13 runs of 10-15 s duration times, measurements in triplicates to derive a standard deviation of all values), while the derived countrate in kcps (mean scattered intensity normalized by the attenuator transmission factor) was used as an indication of the concentration of scattering objects (at a constant aggregation number or size of the scattering objects).

SLS

Multi-angle light scattering measurements (MALS) were performed using an ALV/CG6-8F goniometer, with a 35-mW red helium-neon linearly polarized laser (λ=632.8 nm) and an ALV/LSE-5004 multiple tau digital correlator at 20° C. The data were acquired with the ALV correlator software, the counting time was typically 15 s at each different scattering angles ranging from 30° to 150°, in 5 increments. The radius of gyration ($R_g$) was determined from a Guinier plot resulting from the measurement of the average scattered intensity at the same angles. In addition, the hydrodynamic diameter ($R_h$) was obtained by multi-angle measurement of the main decay rate F (by $2^{nd}$ order Cumulant fitting of the correlogram) at each angle and plot of F as a function of the square of the scattering vector q (defined by the classical formula as a function of the scattering angle, refraction index of water and wavelength of light), in order to derive the translation diffusion constant of the objects and convert it into a hydrodynamic radius using the Stokes-Einstein formula.

TEM

Transmission electron microscopy (TEM) images were recorded using a FEI Tecnai microscope working at 120 kV equipped with an OSIS Megaview II megapixel camera. TEM samples were prepared by depositing 5 μL of the sample solution (1 mg/mL) onto an Agar Scientific Formvar™/carbon 200 mesh copper grid for 1 min, blotted to remove the excess and followed by staining with a 1.5% uranyl acetate solution for 30 s.

3. Drug Encapsulation and Release

Preparation of Drug-Loaded Vesicles

A solution of doxorubicin hydrochloride (Dox-HCl) in 0.9% of aq. NaCl solution (1 mM) was prepared. It was added rapidly (900 μL) to a copolymer (Quino, 2.1 mg) solution in THF. Solvent and excess of doxorubicin was removed by dialysis against 0.9% of aq. NaCl solution (for 2 mL of solution, 2×3 L brine exchange, using a 15 kDa cutoff dialysis membrane). DLS measurements yielded Z-Avg=93 nm, PDI=0.23.

Nanoprecipitation with Hydrophobic v-$Fe_2O_3$ NPs

A suspension (117 μL, 20% feed weight ratio (FWR) iron oxide relatively to polymer, e.g. 0.42 mg) of Beycostat™-coated 4.3±1.1 nm diameter γ-$Fe_2O_3$ VSIONs was added to a solution (100 μL) of block copolymer Quino (2.1 mg) in THF and a solution of Dox-HCl in 0.9% of aq. NaCl solution (1 mM, 783 μL) was added quickly into it. The suspension was dialyzed (15 kDa cutoff) against 0.9% of aq. NaCl solution for 24 h. DLS measurements led to Z-Avg=141 nm, PDI=0.25. Morphology characteristic of polymersomes was observed by TEM.

Fluorimeter Measurements

Release of the encapsulated compound: The amount of released dye was followed at RT by fluorescence spectroscopy (Hitachi F7000 spectrometer). Chemically reduced or irradiated samples were placed in low volume Quartz cuvettes (50 μL) and directly analyzed. The $\lambda_{ex}$ excitation wavelength was set at 480 nm and the emission $\lambda_{em}$ spectra were recorded from 490 to 720 nm. The instrument was used in scan mode, with excitation slit set to 5 nm and emission slit set to 5 nm.

In Vitro Cytotoxicity Studies

The cytotoxicity of Pico-Ps and Pico-Ps(Fe) as well as of Quino-Ps and Quino-Ps(Fe) were evaluated on cancer and healthy cells by the colorimetric MTT assay using 3-(4,5-dimethylthiazolyl-2)-2,5-diphenyltetrazolium bromide as reagent to test the mitochondrial activity of living cells. The cytotoxicity of Pico-Ps and Pico-Ps(Fe) was determined on BWGT3 tumoral hepatocytes and TIB75 healthy hepatocytes chosen as reference cells. Cells were seeded at $2\times10^4$ cells per well in 100 μL of culture medium and were incubated for 24 h at 37° C. in 5% $CO_2$-humified atmosphere. Pico-Ps(Fe) and Pico-Ps polymersomes were incubated for 1 h in serum-free RPMI-1640 culture medium at various concentrations (3 wells per condition, repeated twice). Cells were washed with phosphate buffered saline (PBS) and incubated during 1 h in full culture medium. Absorbance at 480 nm was measured in each well. The viability was calculated by reference to the cells without addition of polymersomes. The half maximum inhibitory concentration leading to 50% cell-viability (IC50) was then calculated by nonlinear regression analysis using GraphPad Prism 6 software (La Jolla, CA, USA).

Five different concentrations (0, 50, 100, 300, and 500 μg/mL) of Pico-Ps(Fe) and Pico-Ps were prepared by dilution of aliquot samples with cell media, respectively. Pico-Ps(Fe) appeared invariably (but only slightly) more toxic than Pico-Ps after 24 h of incubation with TIB75 cells. In contrast, cell-cultures showed almost negligible cytotoxicity of polymersomes on BWTG3 cells even at higher concentrations (up to 500 μg/mL).

Also, the cytotoxicity of quinolinium-derived Ps, Quino-Ps and Quino-Ps(Fe) was studied on epithelial cell line BNL 1ME A.7R.1 (American Type Culture Collection TIB-75). Cells were cultured in 25 mL of Dulbecco's Modified Eagle Medium (DMEM), with a high glucose content (4.5 g/L, GlutaMAX), and were supplemented with 10% fetal calf serum (FCS) and 1% penicillin and streptomycin. Cells were placed in 75 $cm^2$ flasks incubated at 37° C. with 5% $CO_2$ and sub-cultured by Trypsin-0.05% EDTA (4 mL). Cells were plated at a cell density of $2.0\times10^5$ cells per well in a 96-well (100 μL/well) plate and incubated for 24 h at 37° C. under 5% $CO_2$ atmosphere before treatment. After incubation, buffer was replaced by freshly prepared brine (0.9% v/w) and 100 μL of Quino-Ps and Quino-Ps(Fe) were deposited, respectively in three wells, in a triplicated analysis. Cells were incubated further at 37° C. under 5% $CO_2$ atmosphere. After incubation with the polymersomes, the medium was removed and replaced by 100 μL of the MTT reagent (0.5 mg/mL prepared in the culture medium). After 4 h incubation at 37° C. the reagent was carefully removed and 100 μL of DMSO was added to each well in order to dissolve the colored formazan product. Then the plates were shaken on an orbital shaker for 10-15 minute for dissolving the formazan, and the absorbance was measured by using microplate reader (INFINITE® 200 PRO series Tecan) at 562 nm (three replicates were read for each samples). The relative cell viability (%, n=3) was calculated (for both Quino-Ps and Quino-Ps (Fe)) as the percentage of living cells of the treated wells compared to the untreated cells. As before, cell-cultures showed almost negligible cytotoxicity at incubated concentration up to 500 μg/mL for the quinolinium probe based polymersomes, with or without VSION loading.

Figure 1:
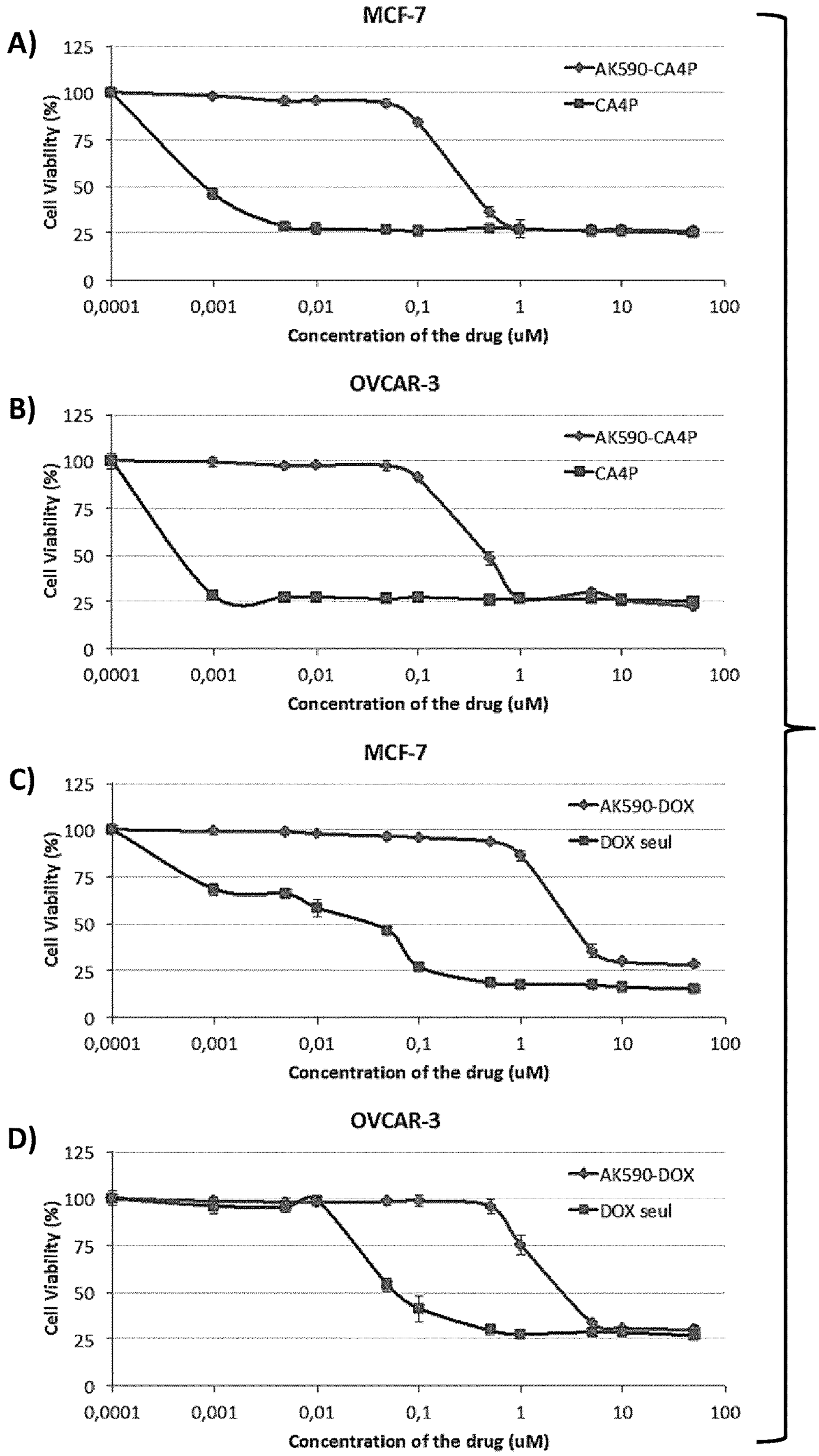
FIG. 1 illustrates the determination of the half maximal inhibitory concentration (IC50) values on MCF-7 human breast cancer (A, C) and Ovar-3 carcinoma cell lines (B, D) for two anticancer APIs, combretastatin (A, B) and doxorubicin (C, D) either encapsulated in Quino-Ps polymersomes or as free API, showing increase of IC50 by 2 to 3 orders of magnitude.

In another series of experiments, the cytotoxicity of combretastatin and doxorubicin-filled Quino-Ps were compared on MCF-7 human breast cancer and Ovar-3 carcinoma cell lines (FIG. 1). As it can be seen, the encapsulated drugs preserve some of their original biological activity/toxicity, although exhibiting 100-1000 times larger values of IC50 of these two APIs compared to the reference (non-encapsulated) compounds. As no leaching of the encapsulated product was evidenced under similar conditions, the reason of the residual biological activity can be the adsorption of a small fraction of the active compound at the surface of the polymersomes in addition to the main part encapsulated inside their lumen. In both cases, these results demonstrate the efficiency of encapsulation in polymersomes to protect healthy tissues as long as they are not subjected to the external or endogenous signal triggering API release.

In Vivo Biodistribution of the Prepared (Un)Loaded Polymersomes

Proton relaxivities of polymersome Pico-Ps(Fe) were measured in saline (9% v/w NaCl). Samples were concentrated to reach 1.0 $mM_{Fe}$ in equivalent iron concentrations (i.e. 0.08 g/L iron oxide) and a series of dilutions were prepared ($c_{Fe}$=1.0, 0.5, 0.2, 0.1, and 0.02 mM). The longitudinal relaxation time ($T_1$) of water protons was measured by saturation-recovery spin-echo sequence (RARE images; echo time TE=13 ms; 10 repetition times TR=15 s, 8 s, 3 s, 1.2 s, 0.800 s, 0.594 s, 0.300 s, 0.144 s, 0.050 s, 0.033 s, repetition time TR=5000 ms, 1500 ms, echo time TE=13 ms) on a 300 MHz MRI scanner (7 T, 30WB, Bruker Biospin) at 25° C., while transversal ($T_2$) relaxation times were measured by a multi spin-echo train acquisition MSME images (TR/TE=15 s/11 ms, 32 echos; 11 to 32×11 ms). $T_2$* relaxation times were measured by using a multi echo gradient echo (GRE) sequence (24 echoes TE=4 ms, TR=5 s).

Figure 2:
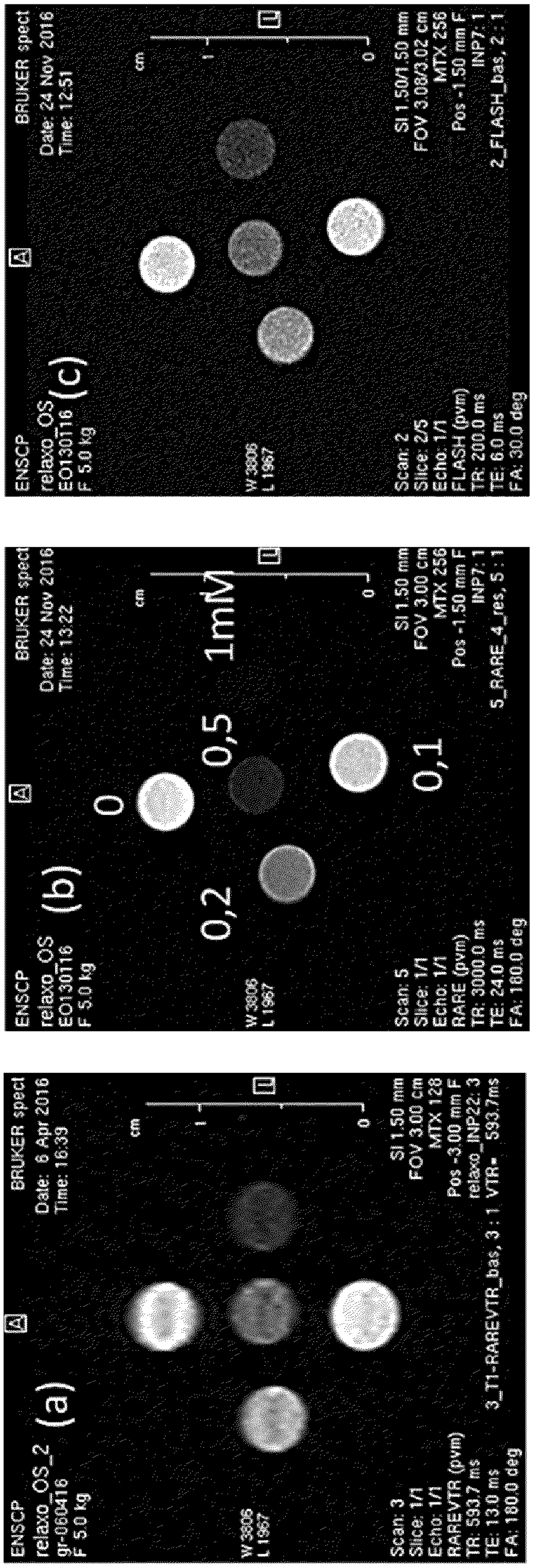
FIG. 2 shows the relaxometric measurements, by using 7T MR images of USPIO-embedding polymersomes by increasing Fe concentrations (0 to 1 mM) in saline (0.9% NaCl). (a) $T_1$ weighted (b) $T_2$ weighted (c) $T_2$* weighted MR Images.

Fields of view of 3×3 $cm^2$, a matrix size of 128×64 and a slice with a thickness of 1.5 mm were used for $T_1$ and $T_2$ maps. For $T_2$ mapping, a field of view of 3×3 $cm^2$, a matrix of 256×192 and a slice with a thickness of 1.5 mm were used. The relaxation rates $1/T_i$ were plotted against iron concentration, and the corresponding longitudinal and transverse relaxivities $r_i$ were obtained by linear regression $1/T_i=(1/T_i)_{buffer}+r_i\ C_{Fe}$ (FIG. 2). Pico-Ps(Fe) exhibits $r_1=0.5\ s^{-1}\cdot mM_{Fe}^{-1}$ in deionized water and $r_1=0.1\ s^{-1}\cdot mM_{Fe}^{-1}$ in physiological saline, respectively as well as $r_2^*=137\ s^{-1}\cdot mM_{Fe}^{-1}$ in DI water and $r_2=43\ s^{-1}\cdot mM_{Fe}^{-1}$ in NaCl, respectively; $r_2^*=119\ s^{-1}\cdot mM_{Fe}^{-1}$ in DI water and $r_2^*=103\ s^{-1}\cdot mM_{Fe}^{-1}$ in NaCl were calculated respectively. The low values of $r_1$ are ascribed to the hydrophobic environment of the VSIONs embedded in the polymersome membranes, impeding any direct "internal sphere" relaxation mechanism of water protons. On the contrary $r_2$ values are pretty high and close to values of commercial MRI contrast agents such as RESOVIST® and CLIAVIST® (discontinued), both of which are magnetic resonance imaging (MRI) contrast agents made of ferucarbotran (iron microparticles coated with carboxydextran), or FERAHEMER a MRI contrast agent made of ferumoxytol (currently on market [Yi-Xiang J Wang, Current status of superparamagnetic iron oxide contrast agents for liver magnetic resonance imaging, World J Gastroenterol. 2015, 21, 13400-13402]) due to the "external sphere" mechanism (i.e. dipolar effect of VSION magnetization working at distance on the water protons) that is enhanced by their clustering within the membranes. Noteworthy, the $(r_2^*/r_1)$ values were high enough to use these magnetic polymer vesicles as negative MRI contrast agents resulting into the "darkening" of specific locations of dynamic susceptibility-enhanced (DSC-MRI) ($T_2^*$) weighted-images in tissues where they accumulate (FIG. 2).

Likewise, the longitudinal and transversal relaxations of Quino-Ps(Fe) were measured by preparing a range of 0.1, 0.2, 0.5 and 1 mM equivalent iron concentrations of suspensions and placing the 5 samples in the MRI spectrometer.

In order to evaluate the contrast agent capacity/efficacy of Quino-Ps(Fe) polymersomes, a sample was compared to a commercial iron oxide contrast agent (Cliavist) chosen as reliable $T_2$ contrast reference. The measured relaxivity ($r_1$, $r_2$) values of Quino-Ps(Fe) VS. CLIAVIST® (same as RESOVIST®) are summarized in Table 1.

TABLE 1

Comparison between the relaxivity values $r_1$ and $r_2$ of iron-based contrast agents, CLIAVIST ® (RESOVIST ®) taken as gold standard, and Quino-Ps(Fe) polymersomes. $R^2$ are the coefficients of determination of the linear fits.

| Relaxivity ($mM^{-1}s^{-1}$) | Cliavist (Resovist) | Quino-Ps(Fe) |
|---|---|---|
| $r_1$ | 2.206 | 0.38 |
| ($R^2$) | (0.99) | (0.99) |
| $r_2$ | 142.4 | 108 |
| ($R^2$) | (0.98) | (0.90) |
| $r_2/r_1$ | 67 | 284 |

Although the longitudinal and transverse relaxivity values $r_1$ and $r_2$ of Quino-Ps(Fe) were somewhat weaker than that of the CLIAVIST®/RESOVIST® due to the very small core size of VSIONs, the combination of their local hydrophobic environment and clustered state in the membranes lead to a Quino-Ps(Fe) sample that is expected to show superior $T_2$ MRI contrast agent proprieties in vivo as the $r_2/r_1$ ratio is as high as 284.

MRI Biodistribution Study on Animal Model

Figure 3:
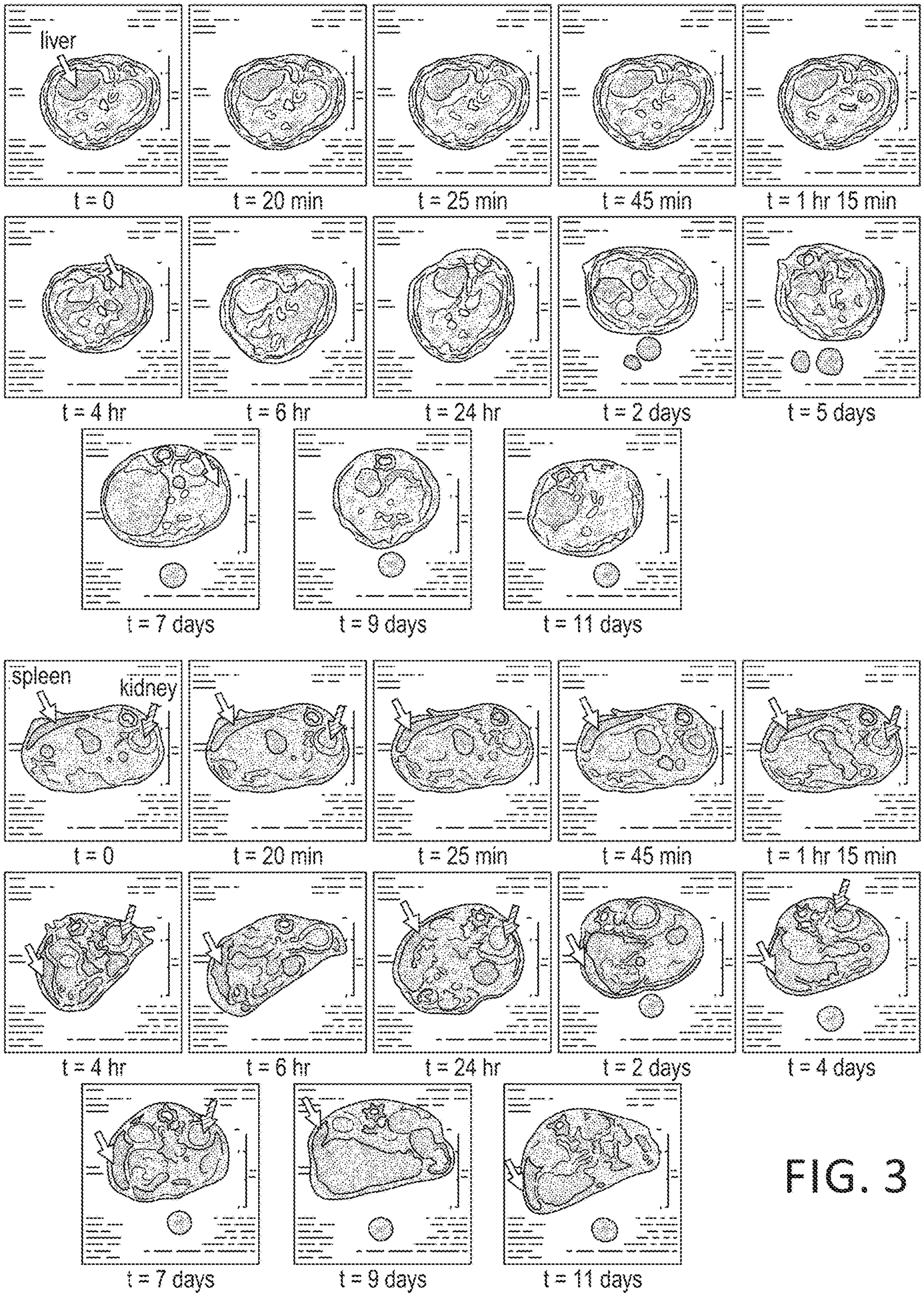
FIG. 3 represents the MRI dynamic susceptibility contrast (DSC) images recorded in living mice at different time points to follow the kinetic uptake and clearance of the magnetic Pico-Ps(Fe) in liver, spleen, kidney, vessels, muscle; (n=3).

For recording the dynamic bio-distribution of Pico-Ps(Fe) in mice under in vivo conditions, a specific protocol, developed by the MR imaging facility, was applied (G. Ramniceanu, B-T. Doan et al, Delayed hepatic uptake of multiphosphonic acid poly(ethylene glycol) coated iron oxide measured by real-time Magnetic Resonance Imaging RSC Advances 2016, 6, 63788-63800). After anesthesia by using 1.5% isoflurane gas in air/$O_2$ mixture (0.5 L/min and 0.2 L/min, respectively), a 30 G catheter was introduced in the caudal vein, and the mouse was installed in a whole-body 40 mm inner diameter RF birdcage coil (Bruker) with a tube of water as a phantom signal reference. A Dynamic Susceptibility Contrast (DSC) imaging methodology was used for the visualization/capture of Pico-Ps(Fe) magnetic polymersomes by the organs. IntraGateFLASH images were recorded to suppress breath motion artefacts in a kinetic way with 3 min duration and with adapted time resolution according to the uptake and clearance of the Pico-Ps(Fe) up to 11 days: TR/TE=90 ms/3 ms, 52 repetitions. Field of view of 3×3 $cm^2$, a matrix size of 256×256, for a 117 μm in-plane resolution, and 5 slices distant of 3 mm with a thickness of 1 mm were used. After 3 reference image acquisitions, 100 μL of Pico-Ps(Fe) (c=1.42 mM of Fe in 0.108 M NaCl 0.9% saline) were injected. The biodistribution and clearance were monitored after injection with 3 min time resolution for 1 h, 4 h, 6 h than daily up to 11 days (FIG. 3).

Biodistribution Study of Qui No-Ps(Fe) in Mice by MRI

The study of the biodistribution of Quino-Ps(Fe) was performed on Balb/c wild type female mice (n=6), aged between 8 to 10 weeks on average. The system was equipped with a temperature-controller set-up, a pneumatic pressure sensor for breathing control, and a face-mask allowing a volatile anesthesia for in vivo imaging of small animals. Mice were anesthetized with 4% isoflurane and kept asleep in the restraining bed during the experiment at a dose of 1.5% and under an oxygen-air mixture (30:70, 0.2 L $min^{-1}$). The respiration was monitored throughout the experiments using a plastic sensor positioned at the chest of the mice and a physiological monitor to monitor the respiration. In parallel, a 5 mm saline tube was introduced to each mouse as a reference "phantom" for the quantification of the MRI signal. The mouse was positioned in a radiofrequency coil and inserted into the MRI spectrometer. A bolus of 200 μL of Quino-Ps(Fe) (c=2.5 mM of Fe) suspension corresponding to 16.6 μmol Fe/kg dose) was injected intravenously (caudal vein) via a 0.38 mm internal and 1.09 mm external diameter catheter, adapted to a 30 G needle.

Figure 6:
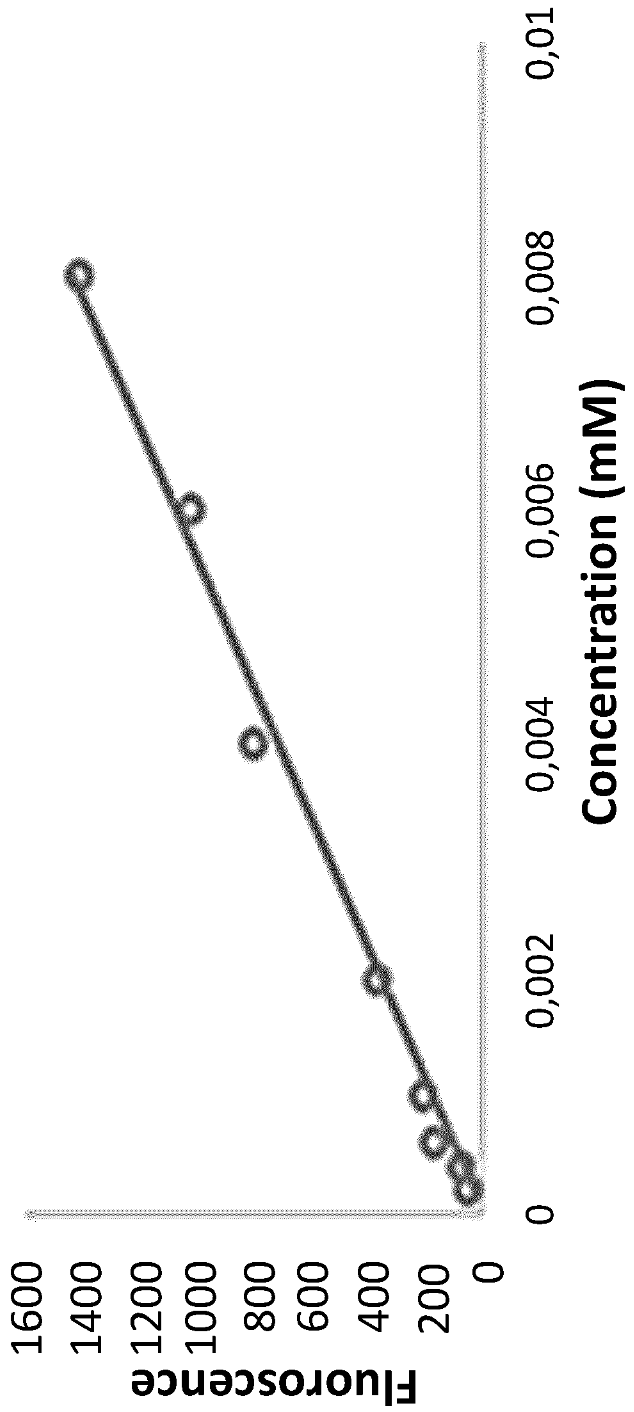
FIG. 6. Calibration curve for the quantification of the doxorubicin release by GSH.
Figure 7:
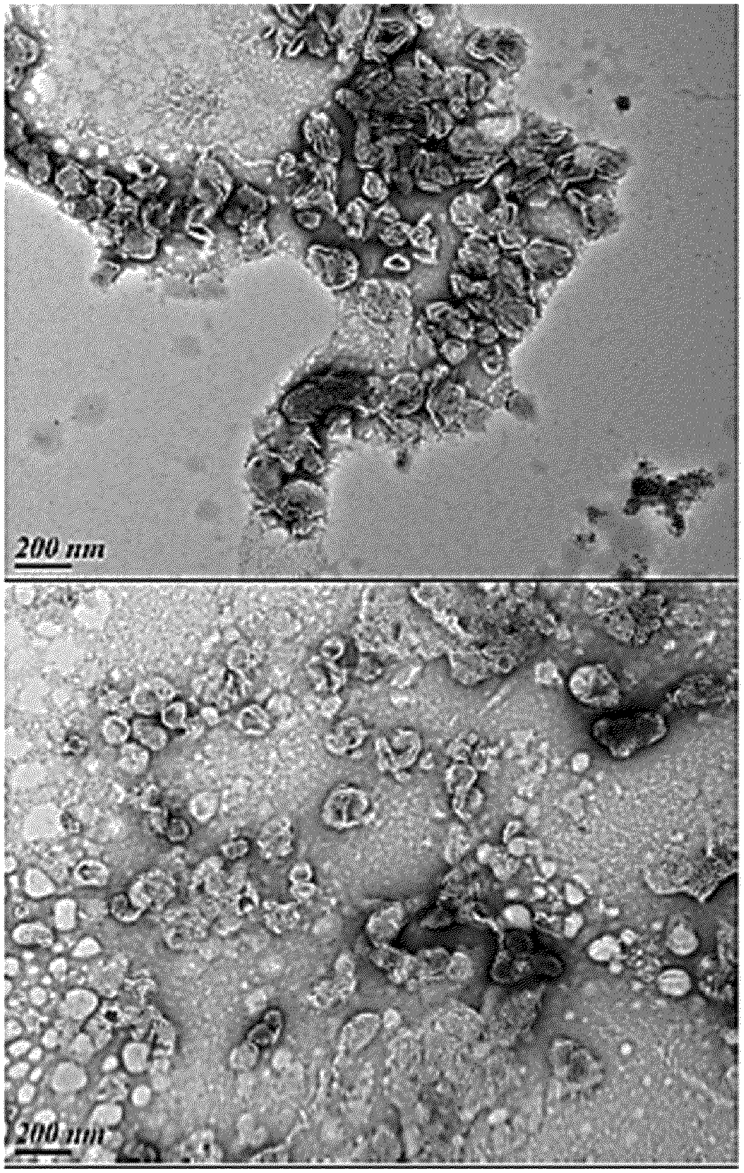
FIG. 7. TEM analysis of Quino-Ps samples after irradiation by the ID17 biomedical beamline at European synchrotron radiation facility (ESRF, Grenoble, France) (conditions.

The kinetic monitoring of the biodistribution in the liver, spleen and kidneys i.e. the capture of the Quino-Ps(Fe) by the reticulo-endothelial system (RES) allowed evaluating their circulation time (FIG. 6). For the MRI analysis, a flash gradient dynamic susceptibility contrast (DSC) echo sequence was used, according to Hoa et al. (Sauramps *Medica,* 2008, Montpellier, France) with the Intragate (Bruker) method that detects the respiratory and cardiac cycles of the mouse during the sequence. A post-processing operation allowed the elimination of the movements and the reconstruction of images without artefacts. This low 30° pulse angle sequence made possible to use short echo (TE=3 ms) and repetition times (TR=90 ms) while maintaining a weighted $T_2^*$ value. The short repetition rate thus allowed high temporal resolution (of 1 min) with good spatial resolution (117×117 $\mu m^2$/pixel) in good sensitivity.

The accumulation of Quino-Ps(Fe) in the organs resulted in decreased MRI signal in $T_2$* weighted sequence, and thus decreased proton $T_2$* relaxation time of the surrounding water. The FLASH-Anatomy sequence set (in the Paravision 5.1 software) allowed the selection of five anatomical slices containing the liver, spleen and kidneys. This sequence used a trigger module to synchronize the acquisition with the breathing trays of the animal, and avoid motion artefacts: IntraGateFLASH sequences of the DSC imaging method were applied to these five slices for 3 min. The study was followed for 1 h (1 scan FLASH IG/10 mn), thus points were acquired after 3 h, 6 h and were more spaced for two weeks. In vivo polymersome tracking was performed by 7T MRI bio-imaging. To follow the kinetics of the capture and clearance of the Quino-Ps(Fe) in the target organs, regions of interest were manually designed on the MRI images (FIG. 6). By this way it was possible to quantify the retention, remanence and elimination in various organs, characteristics for the biodistribution of the Quino-Ps(Fe) imaging agent in vivo (G. Ramniceanu, B-T. Doan et al RSC Advances 2016, 6, 63788-63800).

Figure 4:
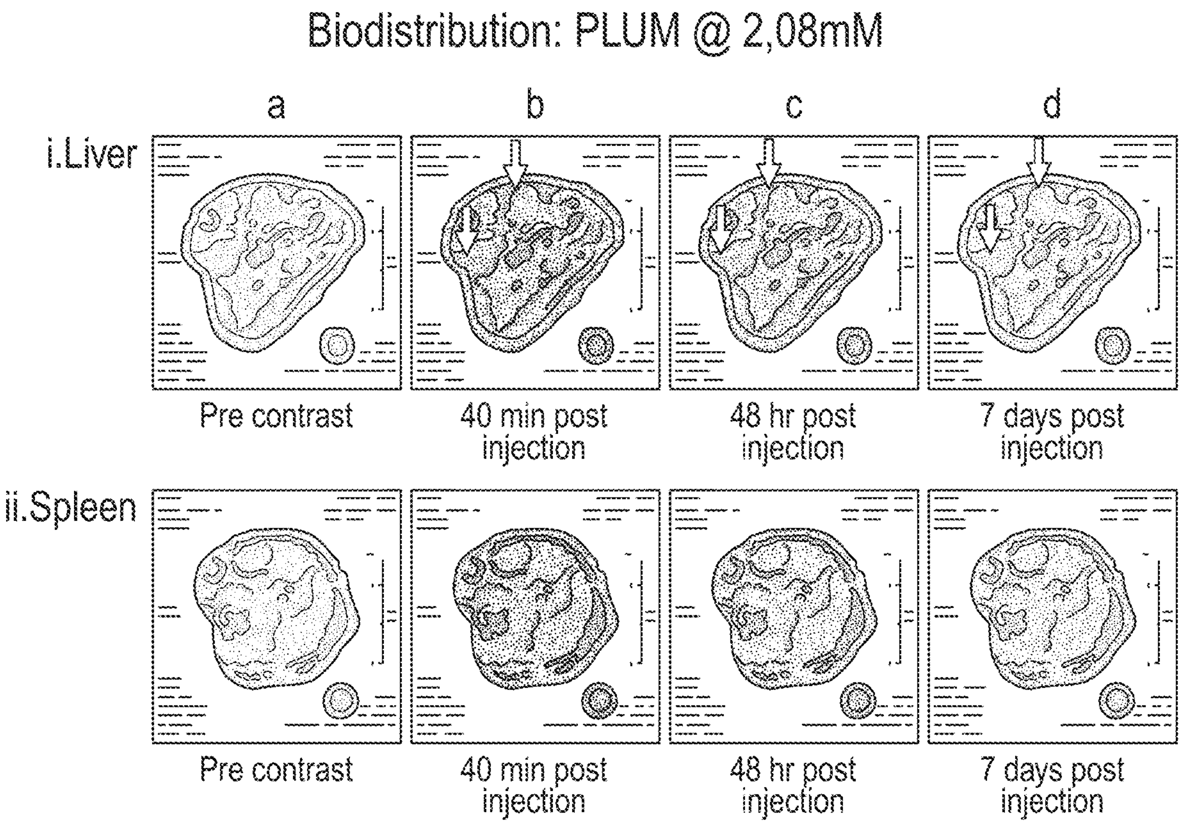
FIG. 4 represents the $T_2$-weighted MR images of mice i. liver and ii spleen recorded a) before and b-d) after injection of Quino-Ps(Fe) (20% FWR) (a) 0 min (b) 40 min, (c) 48 h, (d) 7 days.

Before injection of the bolus of Quino-Ps(Fe) (20% FWR iron oxide), the liver appears as an "iso-signal" on the IntraGateFLASH images with respect to the arteries (FIG. 4). During the hepatic capture of the contrast product, one can notice a hyposignal on the liver MRI sections. Looking at the kidneys (i), the MRI contrast seems visually invariable (weak build-up). Considering the spleen (ii), the picture shows significant hyposignal that persists up to 2 weeks after the injection of the nanoparticles.

As demonstrated by the results reported above, the prepared magnetic polymersomes fulfill the stringent requirements of biocompatibility and stealth properties, parameters that influence diffusion properties and stability under physiological conditions as well as some toxicity issues.

Activation of Polymersomes by Local Electron-Transfer (ET) Using Different Trigger Signals (i.e. Reducing Agents)

The liberation of doxorubicin was followed by monitoring the fluorescence. Fluorescence spectra were collected by excitation at $\lambda_{ex}$=470 nm wavelength and reading at $\lambda_{em}$=600 nm. In order to quantify the encapsulated drug, a method for the quantitative liberation was needed. Different methods, such as solvolysis, photolysis, addition of redox agents (sodium dithionite, mercaptoethanol, sodium thiosulfate, glutathione) were tested and are discussed as follows.

Glutathione (GSH)-Triggered Drug Release from Quino-Ps-DOX

Figure 5:
FIG. 5. Variation of the fluorescence by the treatment of Quino-Ps-DOX with added glutathione (GSH) (10 mM).

In parallel, Quino-Ps-DOX (50 μL) was treated with the natural enzyme glutathione (GSH) in its reduced form, 1 μL at c=10 mM in brine (0.9% (v/w). The concentration of the GSH was set to 10 mM in order to be compatible with the highest intracellular level (FIG. 5).

In the control (blank) experiment, doxorubicin (Dox) solution (50 μL c=1.0 mmol in brine 0.9% (v/w)) was treated with the GSH solution (reduced form, 1.0 μL c=10 mM in brine 0.9% (v/w)): no change in the fluorescence intensity of doxorubicin was observed, indicating that the observed fluorescence variation is not the consequence of a side reaction of GSH with Dox, and also that Dox appears stable under the experimental conditions.

The amount of the liberated drug was quantified by fluorescence ($\lambda_{ex}$=470 nm and $\lambda_{em}$=600 nm), by using a calibration curve (FIG. 6) (y=1.79×$10^5$ ($R^2$=0.9911)). According to this calibration curve, the cumulative liberation of Dox (after "30 min") was approximately 58% by considering that initially 1.0 mM concentration (approx. 544 μg) of drug was used for encapsulation.

Using the calibration curve, the amount of the released drug was calculated as 321 μg. Based on the released amount of drug, a drug loading content (rate of Dox weight over copolymer carrier weight) of 42% and a drug entrapment efficiency (rate of Dox encapsulated over Dox initially added at preparation) of 16% were obtained.

Samples were activated by X/gamma rays as well. Fast fragmentation was observed by using beam of the ID17 biomedical beamline at ESRF synchrotron (Grenoble, France) (conditions: Cuvette: quartz, d (light path): 1 mm, Beam: 120 keV, Bunch length: 48 ps, Bunch repetition rate 5.68 MHz, Dose: 30 Gy). For gamma rays, a conventional medical irradiator in a hospital was used.

Stability on Storage:

Samples were stored at 4° C. An aliquot of each sample (1.0 mL) was analyzed by DLS over 3-4 months repeatedly. Both Quino-Ps (FIG. 8A) and Quino-Ps(Fe) (FIG. 8B) samples appeared stable under the storage conditions (at 4° C.) for 4 months, although a slight Zavg increase with small variation in PDI was observed. Same long term shelf-stability was observed for Pico-Ps and Pico-Ps(Fe) as summarized in Table 2.

TABLE 2

| Sample Name | Measurement Date and Time | T ° C. | Derived Count Rate (kcps) | Z-Ave diameter (nm) | PDI Width (nm) | PDI |
|---|---|---|---|---|---|---|
| NP5_Pico-Ps Reproduced | 9 Sep. 2016 15:48 | 25 | 6064.5 | 120.1 | 41.3 | 0.118 |
| NP5_Pico-Ps Reproduced (Fitrated 0.2 μm) | 9 Sep. 2016 11:55 | 25 | 5715.1 | 118.4 | 40.4 | 0.116 |
| NP5 Pico-Ps (Sterile, in NaCl 9 g/L) | 19 Oct. 2017 15:08 | 25 | 5346.3 | 114.4 | 38.4 | 0.113 |
| NP5 Pico-Ps (NaCl 9 g/L) (Synchrotron irradiation) | 27 Nov. 2017 19:18 | 25 | 5323 | 116.8 | 41.8 | 0.128 |
| NP6 Pico-Ps | 4 Nov. 2016 11:13 | 26.2 | 7985.5 | 145.3 | 85.6 | 0.347 |
| NP6 Pico-Ps (Filtrated 0.2 μm) | 4 Nov. 2016 12:16 | 25 | 4333.5 | 105.1 | 43.2 | 0.169 |

TABLE 2-continued

| Sample Name | Measurement Date and Time | T ° C. | Derived Count Rate (kcps) | Z-Ave diameter (nm) | PDI Width (nm) | PDI |
|---|---|---|---|---|---|---|
| INP7 Pico-Ps(Fe) | 4 Nov. 2016 11:26 | 25 | 18581.3 | 155 | 68.7 | 0.197 |
| INP7 Pico-Ps(Fe) (Filtrated 0.2 μm) | 4 Nov. 2016 12:25 | 25 | 15157.9 | 135.5 | 48.4 | 0.128 |
| INP7_Pico-Ps(Fe) (Conventional irradiation) | 28 Nov. 2016 18:51 | 25 | 16244.7 | 146.9 | 57.4 | 0.153 |
| INP7_Pico-Ps(Fe) (Synchrotron irradiation) | 8 Dec. 2016 17:19 | 25 | 13346.4 | 139 | 55.1 | 0.157 |
| INP7 Pico-Ps(Fe) 1.42 mM Fe NaCl 9 g/L | 19 Oct .2017 14:50 | 25 | 13887.5 | 143 | 58.7 | 0.168 |
| INP7 Pico-Ps(Fe) 1.42 mM Fe NaCl 9 g/L (2nd synchrotron irradiation) | 27 Nov. 2017 19:50 | 25 | 14744 | 143.8 | 53.4 | 0.138 |

Long term stability study of Pico-Ps and Pico-Ps(Fe) samples as assessed by DLS up to one year. Z-Ave diameter and PDI correspond to 2nd order Cumulant analysis of the correlograms, and PDI width is the characteristic broadness of the size distribution calculated by multiplying Z-Ave by the square root of the PDI value. The derived countrate (DCR) is the normalized scattered intensity, which gives indication on the state of aggregation (it increases when colloidal particles are clustered together, or decreases if they are degraded or settle at the bottom of the vial).

Non-Covalent Modification of the Polymersome Bi-Layer by Plasmonic Gold Nanoparticles (GPNP6P) for Fluorescence Tracking, Cancer Diagnosis and Photothermal Therapy.

Gold nanoparticles (GNPs) were prepared according to the method disclosed by Y. Chen et al Nano Lett. 2017, 17, 6330-6334 (DOI: 10.1021/acs.nanolett.7b03070) and were mixed with the picolinium-derived block co-polymer described above in THF. The nano-precipitation was realized by following the above nanoprecipitation procedure and the samples were analyzed by UV-Vis spectrophotometer. Results are illustrated in FIG. 12) and by DLS (Table 3 below). The hydrolytic stability of the prepared GNP-modified NPs (brine 0.9% w/v), stored at 4° C. was followed by DLS (FIG. 13).

TABLE 3

The analysis of GNP-modified picolinium NPs by DLS.

| Conc. of the block co polymer (mg/mL) | Hydrodynamic size (nm) | PDI | Concentration of GNPs (mg/mL) | Zeta potential (mV) |
|---|---|---|---|---|
| 1.0 | 134 | 0.12 | 0.125 | −3.44 |

Further results in respect of GNP6Ps are illustrated in FIGS. 9-11.

FIG. 9 shows that in the SWIR domain (ex: 808 nm, em: LP 1064 nm), PICO-GNP6Ps fluorescence detection was linear from dilution 1 to 1/256. At the highest dilution prepared (1/256), the detection limit was not reached yet (signal/background ratio=2.65). Further, the solution is well detectable by SWIR fluorescence imaging and will allow efficient detection in vivo in mice. PICO-GNP6Ps were well detectable by SWIR fluorescence imaging with enough sensitivity to consider detection in vivo in mice.

Pharmacokinetics of PICO-GNP6Ps was carried out in vivo in mice (FIG. 10): It was found that following intravenous injection, PICO-GNP6Ps display a short circulation time in the bloodstream: As soon as 1 h post injection there is almost no more signal circulating in the bloodstream, with a half-life (Diffusion+elimination) of 2.31 min and a pure elimination half-life of 18.48 min.

The intravenous injection of 200 μL of PICO-GN6Ps in mice led to:

No visible signs of discomfort during injection in healthy mice,

No visible signs of pain or suffering during the awakening phase of the mice,

Normal behavior of the mice up to 48 h post injection.

As illustrated in FIG. 11, SWIR fluorescence imaging over 48 hours shows a strong liver signal as early as 1 hour. This signal decreases along time but remains significant at 48 h post injection. Some fluorescence signal is also observed in the spleen but no further uptake is identified in vivo by noninvasive fluorescence imaging.

The invention claimed is:

1. A photo- or redox-cleavable amphiphilic copolymer compound of formula (I):

(I)

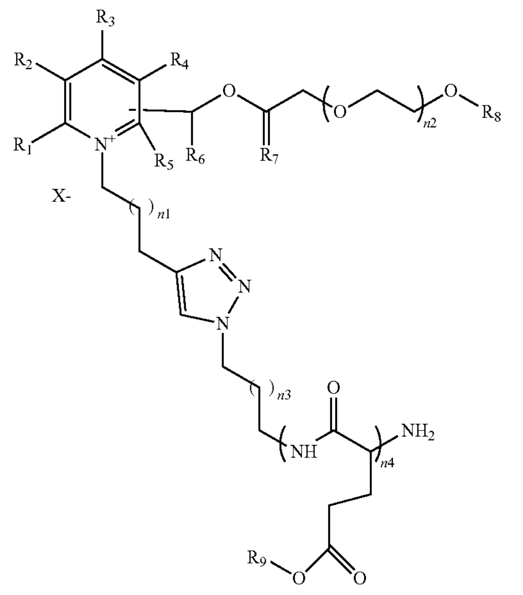

wherein the side chain in formula (1) designated as

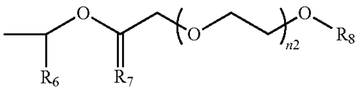

is connected to one substitution group on the pyridinium ring selected from $R_1$, $R_2$, $R_3$ $R_4$ and $R_5$ substitution groups, and a remainder of the $R_1$, $R_2$, $R_3$ $R_4$ and $R_5$ substitution groups on the pyridinium ring are selected from the group consisting of H, OH, OMethyl, CN, NRR', $NO_2$ halogen, R and R' are identical or different and are independently chosen from H, phenyl or a methyl group, or two adjacent $R_1$, $R_2$, $R_3$ $R_4$ and $R_5$ are linked together to form one or more aromatic rings fused with the pyridinium ring to which they are attached so as to form an optionally substituted bi-cyclic quinolinium or optionally substituted fused tri-cyclic N-containing heteroaryl, $R_6$ is H or an alkyl group;

$R_7$ is O, or alkylene, $R_8$ and $R_9$ identical or different are independently chosen from H, alkyl, aryl or benzyl;

wherein the optional substituents are selected from the group consisting of OH, OMethyl, CN, $NO_2$, NRR', halogen;

R and R' are identical or different and are independently chosen from H, phenyl or a methyl group;

$n_1$ and $n_3$ are identical or different integers comprised between 0 and 5 defining the length of the spacer;

$n_2$ is an integer comprised between 34 and 80 denoting the polymerization degree of ethylene oxide in the hydrophilic block of the amphiphilic copolymer;

$n_4$ is an integer chosen between 18 and 40 denoting the polymerization degree of γ-$R_9$-L-glutamate in the hydrophobic block of the amphiphilic copolymer;

$X^-$ is a halide or a trifluoromethanesulfonate (OTf), phosphate, sulfate, perchlorate or nitrate counterion.

2. The photo- or redox-cleavable amphiphilic copolymer compound of formula (I) according to claim 1 chosen from:

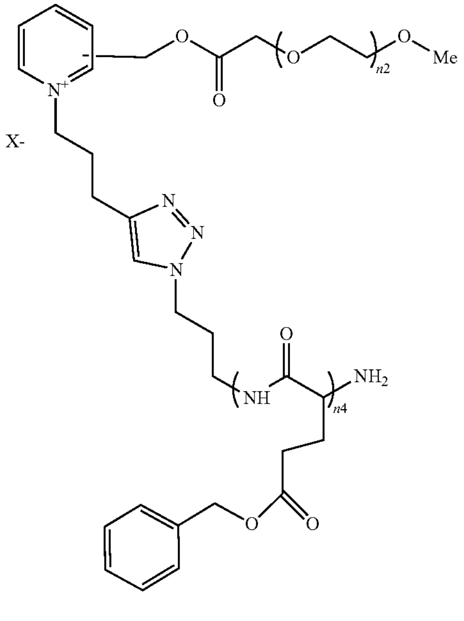

-continued or

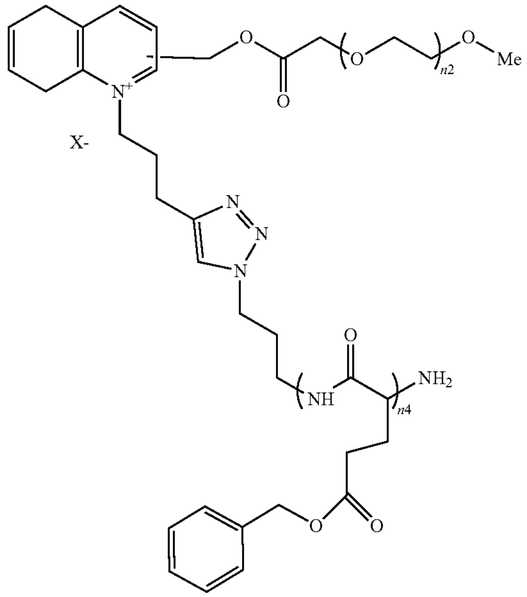

where $X^-$ is a halide or a trifluoromethanesulfonate (OTf), and n2 and n4 are defined as in claim 1.

3. A polymersome comprising an amphiphilic bilayer, wherein the amphiphilic bilayer of said vesicle comprises a photo-cleavable or redox-cleavable amphiphilic copolymer compound according to claim 1.

4. The polymersome according to claim 3, wherein the polymersome further comprises a mineral, a metal, a semi-metal, or an oxide or other chalcogenide nanoparticle embedded into said polymersome membrane.

5. The polymersome according to claim 4 wherein said mineral, metal or semi-metal, oxide or chalcogenide is chosen with constituent from the periodic table of the elements with an atomic number greater than 21.

6. The polymersome according to claim 4 wherein said mineral, metal or semi-metal, oxide or chalcogenide nanoparticle is an ultra-small iron oxide nanoparticle (USPIO), a superparamagnetic iron oxide nanoparticle (SPION), a very small iron oxide nanoparticles (VSION), a hafnium-oxide, an iron-bismuth or iron-platinum alloy, a gadolinium oxide, a dysprosium oxide, a bismuth selenide or bismuth telluride, silver, platinum, or a gold nanoparticle or atom cluster.

7. The polymersome according to claim 3 further comprising an active pharmaceutical ingredient (API), said API being encapsulated within either aqueous internal compartment or within hydrophobic membrane of said polymersome.

8. The polymersome according to claim 7, wherein said API is suitable for the treatment of cancers, inflammation, diabetes, bacterial infections, viral infections, or orphan diseases.

9. An aqueous suspension comprising polymersomes according to claim 3.

10. A pharmaceutical composition or a medical device comprising an aqueous suspension according to claim 9.

11. A process of preparation of the copolymer according to claim 1 comprising the step of reacting a compound of formula (II):

(II)

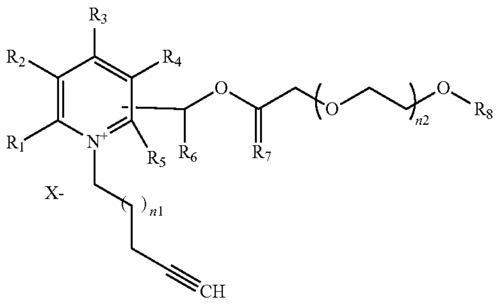

with a compound of formula (III):

(III)

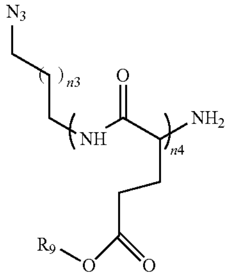

wherein $R_1$, $R_2$, $R_3$, $R_4$, $R_5$, $R_6$, $R_7$, $R_8$, $R_9$, R, X, $n_1$, $n_2$ $n_3$ and $n_4$ are defined as in claim 1.

12. Process of preparation of the suspension of polymersomes according to claim 3 comprising:

Optionally mixing a compound of formula (I) with a hydrophobically coated mineral, metal or semi-metal, oxide or chalcogenide nanoparticle suspension and/or an API in an organic solvent miscible with water, Self-assembly by nanoprecipitation of the polymersome vesicles in an aqueous solution (also called "solvent-shift" method), optionally followed by dialysis of the suspension or heating to remove any trace of organic solvent.

* * * * *